(12) United States Patent
Welker-Nieuwoudt et al.

(10) Patent No.: US 9,238,217 B2
(45) Date of Patent: Jan. 19, 2016

(54) CATALYST FOR PREPARATION OF AN UNSATURATED CARBOXYLIC ACID BY GAS PHASE OXIDATION OF AN UNSATURATED ALDEHYDE

(71) Applicant: BASF SE, Ludwigshafen (DE)

(72) Inventors: Cathrin Alexandra Welker-Nieuwoudt, Birkenheide (DE); Cornelia Katharina Dobner, Ludwigshafen (DE); Holger Borchert, Offstein (DE); Ulrich Hammon, Mannheim (DE); Josef Macht, Antwerp (BE); Andrey Karpov, Cranford, NJ (US); Christian Walsdorff, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/487,383

(22) Filed: Sep. 16, 2014

(65) Prior Publication Data
US 2015/0080605 A1    Mar. 19, 2015

Related U.S. Application Data

(60) Provisional application No. 61/878,651, filed on Sep. 17, 2013.

(30) Foreign Application Priority Data

Sep. 17, 2013  (DE) .................. 10 2013 218 628

(51) Int. Cl.
| | |
|---|---|
| C07C 51/235 | (2006.01) |
| B01J 23/888 | (2006.01) |
| B01J 37/04 | (2006.01) |
| B01J 37/08 | (2006.01) |
| B01J 35/02 | (2006.01) |
| B01J 35/10 | (2006.01) |
| B01J 37/00 | (2006.01) |
| B01J 35/04 | (2006.01) |
| C07C 51/25 | (2006.01) |
| B01J 37/02 | (2006.01) |
| B01J 23/94 | (2006.01) |
| B01J 35/00 | (2006.01) |
| B01J 23/00 | (2006.01) |
| B01J 23/887 | (2006.01) |

(52) U.S. Cl.
CPC ............ B01J 23/8885 (2013.01); B01J 23/002 (2013.01); B01J 23/8877 (2013.01); B01J 23/94 (2013.01); B01J 35/002 (2013.01); B01J 35/0006 (2013.01); B01J 35/023 (2013.01); B01J 35/04 (2013.01); B01J 35/108 (2013.01); B01J 35/1071 (2013.01); B01J 35/1076 (2013.01); B01J 37/0009 (2013.01); B01J 37/0045 (2013.01); B01J 37/0223 (2013.01); B01J 37/0232 (2013.01); B01J 37/04 (2013.01); B01J 37/08 (2013.01); C07C 51/235 (2013.01); C07C 51/252 (2013.01); B01J 35/008 (2013.01); B01J 35/1004 (2013.01); B01J 35/1033 (2013.01); B01J 35/1038 (2013.01); B01J 35/1066 (2013.01); B01J 37/0018 (2013.01); B01J 37/0036 (2013.01); B01J 2523/00 (2013.01); Y10T 428/249953 (2015.04)

(58) Field of Classification Search
None
See application file for complete search history.

(56) References Cited

U.S. PATENT DOCUMENTS

| 3,147,084 A | 9/1964 | Franzen et al. |
|---|---|---|
| 2003/0181762 A1 | 9/2003 | Machhammer et al. |
| 2004/0015013 A1 | 1/2004 | Hammon et al. |
| 2004/0249196 A1 | 12/2004 | Dieterle et al. |
| 2005/0261517 A1 | 11/2005 | Dieterle et al. |
| 2007/0041795 A1 | 2/2007 | Neto et al. |

(Continued)

FOREIGN PATENT DOCUMENTS

| DE | 2 201 528 | 11/1972 |
|---|---|---|
| DE | 21 35 620 | 1/1973 |

(Continued)

OTHER PUBLICATIONS

International Search Report issued Feb. 26, 2015 in PCT/EP2014/069580 filed Sep. 15, 2014.

(Continued)

*Primary Examiner* — Yevegeny Valenrod
(74) *Attorney, Agent, or Firm* — Oblon, McClelland, Maier & Neustadt, L.L.P.

(57) ABSTRACT

What is described is a catalyst for preparation of an $\alpha,\beta$-unsaturated carboxylic acid by gas phase oxidation of an $\alpha,\beta$-unsaturated aldehyde, comprising a shaped support body with an active composition applied thereto, wherein the active composition coverage q $$q = \frac{Q}{(100 - Q)S_m}$$

is at most 0.3 mg/mm², where Q is the active composition content of the catalyst in % by weight and $S_m$ is the specific geometric surface area of the shaped support body in mm²/mg. Also described are a process for preparing the catalyst and a process for preparing an $\alpha,\beta$-unsaturated carboxylic acid by gas phase oxidation of an $\alpha,\beta$-unsaturated aldehyde over a fixed catalyst bed comprising a bed of the catalyst. The catalyst, with constantly high conversion of acrolein, reduces overoxidation to $CO_x$ and increases the selectivity of acrylic acid formation.

16 Claims, 14 Drawing Sheets

(56) References Cited

U.S. PATENT DOCUMENTS

| | | |
|---|---|---|
| 2012/0095267 A1 | 4/2012 | Macht et al. |
| 2014/0018572 A1 | 1/2014 | Welker-Nieuwoudt et al. |
| 2014/0221683 A1 | 8/2014 | Welker-Nieuwoudt et al. |

FOREIGN PATENT DOCUMENTS

| | | |
|---|---|---|
| DE | 28 30 765 A1 | 1/1980 |
| DE | 29 03 582 A1 | 8/1980 |
| DE | 29 09 671 A1 | 10/1980 |
| DE | 25 13 405 C2 | 10/1982 |
| DE | 199 27 624 A1 | 12/2000 |
| DE | 100 28 582 A1 | 12/2001 |
| DE | 103 60 057 A1 | 7/2004 |
| DE | 10 2004 025 445 A1 | 2/2005 |
| DE | 103 50 822 A1 | 6/2005 |
| DE | 10 2005 010 645 A1 | 8/2005 |
| DE | 10 2007 010 422 A1 | 9/2008 |
| DE | 10 2010 048 405 A1 | 5/2011 |
| DE | 10 2013 202 048 A1 | 4/2013 |
| EP | 0 383 224 A2 | 8/1990 |
| EP | 0 714 700 A2 | 6/1996 |
| EP | 0 873 783 A1 | 10/1998 |
| WO | WO 95/11081 A1 | 4/1995 |
| WO | WO 2004/085370 A1 | 10/2004 |
| WO | WO 2005/030380 A2 | 4/2005 |
| WO | WO 2011/134932 A1 | 11/2011 |

OTHER PUBLICATIONS

German Search Report issued May 28, 2014 in 10 2013 218 628.2 filed Sep. 17, 2013.

CATALYST FOR PREPARATION OF AN UNSATURATED CARBOXYLIC ACID BY GAS PHASE OXIDATION OF AN UNSATURATED ALDEHYDE

Catalysts composed of a shaped support body and a shell of catalytically active oxide composition which comprises at least the elements Mo, V and Cu and has been applied to the outer surface of the support body are known (cf., for example EP-A 714 700, DE-A 199 27 624, DE-A 10360057 and WO 2011/134932 A1). They are used principally as catalysts for the heterogeneously catalyzed partial gas phase oxidation of acrolein to acrylic acid.

However, these catalysts have disadvantages. When used as catalysts for the heterogeneously catalyzed partial gas phase oxidation of acrolein to acrylic acid, the selectivity of acrylic acid formation is not entirely satisfactory. A particular side reaction which occurs is overoxidation to CO and $CO_2$ (referred to collectively hereinafter as $CO_x$).

When the prior art catalysts are used, a sufficiently high conversion of acrolein is often achieved only under conditions under which the selectivity of acrylic acid formation is unsatisfactory. Thus, at the temperatures under which a sufficiently high conversion of acrolein is achieved, there is frequently overoxidation and consequently a reduction in the selectivity of acrylic acid formation.

WO 2011/134932 discloses an eggshell catalyst consisting of a hollow cylindrical support body and a shell of catalytically active oxide composition applied to the outer surface of the support body, and a process for preparing acrylic acid by catalytic oxidation of acrolein in the gas phase over a fixed catalyst bed comprising the eggshell catalyst. In the working examples, after 100 hours of operation, selectivities of acrylic acid formation of up to 97.5% are achieved.

The problem addressed was that of providing a catalyst with which, with constantly high conversion of acrolein, overoxidation to $CO_x$ can be reduced and the selectivities of acrylic acid formation can be increased.

This problem is solved by a catalyst for preparation of an α,β-unsaturated carboxylic acid by gas phase oxidation of an α,β-unsaturated aldehyde, comprising a shaped support body with an active composition applied thereto, wherein the active composition coverage q $$q = \frac{Q}{(100-Q)S_m}$$

is at most 0.3 mg/mm$^2$, where Q is the active composition content of the catalyst in % by weight and $S_m$ is the specific geometric surface area of the shaped support body in mm$^2$/mg.

Preferably, the active composition coverage q is at most 0.26 mg/mm$^2$, preferably at most 0.22 mg/mm$^2$. In general, the active composition coverage q is at least 0.10 mg/mm$^2$, preferably at least 0.15 mg/mm$^2$.

The shaped support body preferably has a defined geometric shape.

Preferred shaped support bodies are rings, spheres, tablets, punched tablets, trilobes, punched trilobes, star extrudates, star tablets, wagonwheels, extrudates, pills, cylinders and hollow cylinders. The longest dimension (i.e. the longest direct straight line connecting two points on the shaped body surface) of the shaped support body is advantageously 1 to 10 mm.

Particularly preferred shaped support bodies are hollow cylinders. The hollow cylindrical shaped support body preferably has a height of 2 to 5 mm and an external diameter of 4 to 8 mm, the median difference of the external diameter and internal diameter being 1 to 2 mm. The median difference of the external diameter and internal diameter corresponds to the wall thickness. Particular preference is given to a geometry having an external diameter of 7 mm, a height of 3 mm and an internal diameter of 4 mm.

The shaped support body preferably consists of inert material. "Inert" means that the material of the shaped support body does not change significantly under the conditions of the gas phase oxidation and has at most a negligible catalytic activity, if any, compared to the active composition applied with respect to the gas phase oxidation. Useful inert materials include especially aluminum oxide, silicon dioxide, silicon carbide, zirconium dioxide, thorium dioxide, silicates such as clay, kaolin, steatite, pumice, aluminum silicate and magnesium silicate, and mixtures thereof. Steatite is preferred. Steatite of the C 220 type is particularly preferred. Very particular preference is given to steatite of the C 220 type from CeramTec.

Preferably, the hollow body has distinct surface roughness (e.g. hollow cylinder with grit layer). Advantageously, the surface of the hollow cylindrical shaped support body is rough, since an elevated surface roughness generally results in an increased bond strength of the shell of active composition and/or precursor composition applied to the surface of the hollow cylindrical shaped support body. The surface roughness $R_z$ is preferably 30 to 60 μm, more preferably 40 to 50 μm (determined to DIN 4768 Sheet 1 with a "Hommel Tester for DIN-ISO surface parameters" from Hommelwerke).

The inert material may be porous or nonporous. Preferably, the inert material is essentially nonporous (the total volume of the pores, based on the volume of the support body, is less than 1% by volume). The geometric density of the inert material is generally in the range from 0.5 to 8.0 g/cm$^3$, preferably 1.0 to 7.0 g/cm$^3$, further preferably 1.5 to 6.0 g/cm$^3$, more preferably 2.0 to 5.0 g/cm$^3$. The geometric density of the chemically inert material is calculated by dividing the mass of the shaped support body by the geometric volume thereof.

The geometric volume can be calculated from corresponding measurements for the perfect underlying geometric forms. For example, the geometric volume of a hollow cylinder can be calculated on the basis of the height H of the cylinder, the external diameter ED and the diameter of the inner bore ID.

The active composition content Q (in % by weight) of the catalyst is the mass of the active composition, based on the sum of the masses of active composition and shaped support body. To determine the mass of the active composition, the known mass of the shaped support body can be subtracted from the mass of a catalyst determined by weighing (after the heat treatment for removal of the binder; see below). To increase the measurement accuracy, the mass of a multitude of catalysts or shaped support bodies can be determined and averaged. For instance, the mass of the active composition of a defined number of catalysts can be determined by determining the total mass of the catalysts and subtracting the shaped support body weight, which is found from multiplication of the shaped support body weight by the number of shaped support bodies. The determination of the active composition content Q is also possible by washing the active composition off the shaped support body. For this purpose, the coated catalyst can, for example, be boiled repeatedly with aqueous ammonia solution and the resulting liquid can be decanted off. The remaining support can subsequently be dried. The active composition content is calculated from the difference between catalyst mass (determined before washing off the active composition) and support mass (determined after washing off the active composition and drying) based on the catalyst mass.

The support material content of the catalyst in % by weight is accordingly (100-Q).

The specific geometric surface area of the shaped support body $S_m$ is the geometric surface area of the shaped support body based on the mass of the shaped support body.

The geometric surface area can be calculated from corresponding measurements for the perfect underlying geometric forms. The geometric surface area is an idealized parameter and does not take account of the increase in surface area caused by the porosity or surface roughness of the shaped bodies.

In the case of a spherical shaped support body, the geometric surface area is $$4\pi r^2$$

where r is the radius of the spherical shaped support body. In the case of a hollow cylindrical shaped support body, the geometric surface area is $$\frac{\pi}{2}((ED)^2 - (ID)^2) + \pi(ED + ID)H$$

where H is the height, ED is the external diameter and ID is the internal diameter of the hollow cylindrical shaped support body.

Preferably, the mean thickness of the active composition applied to the shaped support body is 50 to 400 μm, preferably 75 to 350 μm, more preferably 100 to 300 μm and most preferably 100 to 200 μm.

Preferably, the thickness of the active composition applied to the shaped support body is of maximum homogeneity. The thickness of the active compositions applied is likewise of maximum homogeneity between various shaped support bodies.

Active compositions for preparation of an α,β-unsaturated carboxylic acid by gas phase oxidation of an α,β-unsaturated aldehyde are known per se. For example, catalytically active multielement oxide compositions comprising the elements Mo and V are suitable, where the molar proportion of the element Mo in the total amount of all elements other than oxygen in the catalytically active multielement oxide composition is 20 mol % to 80 mol %, the molar ratio of Mo present in the catalytically active multielement oxide composition to V present in the catalytically active multielement oxide composition, Mo/V, is 15:1 to 1:1. Preferably, the multielement oxide also comprises at least one of the elements Nb and W; the corresponding molar ratio Mo/(total amount of W and Nb) is preferably 80:1 to 1:4. Frequently, such multielement oxide compositions also comprise Cu in a corresponding molar ratio of Mo/Cu of 30:1 to 1:3.

The aforementioned multielement oxide compositions may, as well as the elements Mo, V, and optionally Nb and/or W or Cu, additionally comprise, for example, the elements Ta, Cr, Ce, Ni, Co, Fe, Mn, Zn, Sb, Bi, alkali metal (Li, Na, K, Rb, Cs), H, alkaline earth metal (Mg, Ca, Sr, Ba), Si, Al, Ti and Zr. Of course, the multielement oxide active composition may also consist solely of the elements Mo, V, O, and also Cu and optionally W and/or Nb. They are especially suitable as active compositions for catalysts for heterogeneously catalyzed partial gas phase oxidation of acrolein to acrylic acid.

Compositions of very particular suitability as active compositions for catalysts for heterogeneously catalyzed partial gas phase oxidation of acrolein to acrylic acid comprise a multielement oxide composition of the following general formula (I)

$$Mo_{12}V_aX^1_bX^2_cX^3_dX^4_eX^5_fO_n \qquad (I)$$

in which $X^1$ is W, Nb, Ta, Cr and/or Ce,
$X^2$ is Cu, Ni, Co, Fe, Mn and/or Zn,
$X^3$ is Sb and/or Bi,
$X^4$ is one or more alkali metals and/or alkaline earth metals and/or N,
$X^5$ is Si, Al, Ti and/or Zr,
a is a number in the range from 1 to 6,
b is a number in the range from 0.2 to 4,
c is a number in the range from 0 to 18, preferably from 0.5 to 18,
d is a number in the range from 0 to 40,
e is a number in the range from 0 to 4,
f is a number in the range from 0 to 40, and
n is the stoichiometric coefficient of the element oxygen, which is determined by the stoichiometric coefficients of the elements other than oxygen and the valency thereof in (I).

preferably, the variables should be selected within the ranges specified with the proviso that the molar proportion of the element Mo in the total amount of all elements other than oxygen in the multielement oxide composition (I) is 20 mol % to 80 mol %.

The multielement oxide composition preferably corresponds to the general formula (II)

$$Mo_{12}V_aW_bCU_cX^4_eX^5_fO_n \qquad (II)$$

in which $X^4$ is one or more alkali metals and/or alkaline earth metals,
$X^5$ is one or more elements from the group of Si, Al, Ti and Zr,
a is a number in the range from 2 to 4, advantageously a number in the range from 2.5 to 3.5,
b is a number in the range from 0 to 3, advantageously a number in the range from 0.2 to 3, preferably a number in the range from 0.5 to 2, more preferably a number in the range from 0.75 to 1.5,
c is a number in the range from 0.5 to 3, advantageously a number in the range from 0.7 to 2.7, preferably a number in the range from 0.9 to 2.4, more preferably a number in the range from 1 to 1.5,
e is a number in the range from 0 to 4, advantageously a number in the range from 0 to 2, preferably a number in the range from 0 to 1, more preferably a number in the range from 0 to 0.2,
f is a number in the range from 0 to 40, advantageously a number in the range from 0 to 15, preferably a number in the range from 0 to 8, more preferably 0, and
n is the stoichiometric coefficient of the element oxygen, which is determined by the stoichiometric coefficients of the elements other than oxygen and the valency thereof in (II).

Elements $X^4$ and $X^5$ are not necessarily part of the active composition of the general formula (II). They act generally as inert diluents within the active composition. The incorporation thereof into the active composition can adjust the volume-specific catalyst activity to a desired level.

In one embodiment, the active composition may be in the form of a finely divided mixture of the multielement oxide composition comprising the elements Mo and V, for example of the formula I or II, with a molybdenum oxide source, as described in DE 10 2007 010 422. The molybdenum oxide source is suitably selected from oxides of molybdenum and compounds of molybdenum from which an oxide of molybdenum forms under the action of elevated temperature and molecular oxygen. These include molybdenum oxides such as $MoO_3$, $Mo_{18}O_{52}$, $Mo_8O_{23}$ and $Mo_4O_{11}$, or compounds such as ammonium molybdate $[(NH_4)_2MoO_4]$ and the ammonium polymolybdates such as ammonium heptamolybdate tetrahydrate $[(NH_4)_6Mo_7O_{24} \cdot 4H_2O]$. An alternative example is molybdenum oxide hydrate ($MoO_3 \cdot xH_2O$). $MoO_3$ is a preferred molybdenum oxide source.

The granularity (particle diameter, or particle diameter distribution) of the finely divided molybdenum source is, advantageously in accordance with the invention, identical to that of the finely divided multielement oxide comprising the elements Mo and V (this enables particularly homogeneous mixing with the finely divided muiltielement oxide). This is especially true when the finely divided molybdenum oxide source is a molybdenum oxide (especially $MoO_3$).

The additional use of the molybdenum oxide source can preventively counteract the deactivation of the catalyst in the course of a heterogeneously catalyzed partial gas phase oxidation of acrolein into acrylic acid, or delay the onset of deactivation.

In general, the catalyst is porous. The catalyst preferably has a particular distribution of pores of particular mean diameters. The proportion by volume $p_{vol}$ of macropores in the catalyst is preferably at least 0.35, where is determined by $$p_{vol} = \frac{V_{0.26-2}}{V_{0.02-6.5}}$$

in which
$V_{0.26-2}$ is the volume of the pores having mean diameters in the range from 0.26 to 2 μm, and
$V_{0.02-6.5}$ is the volume of the pores having mean diameters in the range from 0.02 to 6.5 μm.

The volume of the pores having mean diameters in the nanometer and micrometer range can be determined by mercury porosimetry (for example to DIN No. 66133). Mercury behaves as a non-wetting liquid with respect to most solids. Therefore, mercury is not spontaneously absorbed by the porous material but penetrates into the pores of the solid sample only under an external pressure. The level of this pressure depends on the size of the pores. This behavior is exploited in mercury porosimetry in order to find the pore diameter via the intrusion in volumetric terms at an externally applied pressure.

This is done by immersing the porous system (the sample to be analyzed) which has been outgassed beforehand (in order to outgas any liquid present in the porous structure) into a mercury bath, the pressure of which can be altered.

Since the mercury does not wet the sample material, the mercury has to be forced into the pores of the sample (establishment of equilibrium is awaited at the respective pressure). The penetration of the mercury into pores having greater surface area proceeds at comparatively lower pressures, while the penetration of the mercury into narrower pores requires a comparatively higher pressure. Assuming the presence of circular cylindrical pores, with the aid of the Washburn equation, the external pressure required to force the liquid mercury into the pores of appropriate diameter (to intrude; mercury intrusion) against the surface tension of the mercury can be related to said diameter. The pressure range employed in the course of the mercury porosimetry analysis correlates to the range of pore diameters covered.

The mercury intrusion curves determined experimentally at 25° C. can subsequently be used to extract, by calculation, over the range of pore diameters covered, the diameter distribution of the pores, the total internal surface are of the pores and the total internal volume of the pores (the total intrusion volume; the total pore volume) (cf. inaugural thesis "Eigenschaften and Einsatzmöglichkeiten von Aerogelfenstern im Vergleich mit konventionellen sowie evakuierten Fenstern" [Properties and Possible Uses of Aerogel Windows Compared to Conventional and Evacuated Windows] by Georges Reber (1991), at the faculty of philosophy and natural sciences of the University of Basle). The Micromeritics Auto Pore IV 9520 measuring instrument described hereinafter comprises standard calculation programs suitable for these purposes.

An inventive catalyst is generally obtained by applying a pulverulent active composition to a shaped support body, preferably by the preparation processes described hereinafter.

The pulverulent active composition can be prepared in different ways. In one embodiment, the active composition is prepared by using sources of elemental constituents of the active composition to produce an intimate dry mixture which is calcined at temperatures of 350 to 600° C. and then converted to powder form.

Preferred sources of the elemental constituents of the active composition are oxides of metals present in the active composition. Useful sources of the elemental constituents of the active composition also include compounds which can be converted to oxides by heating, at least in the presence of oxygen; especially halides, nitrates, formates, oxalates, citrates, acetates, carbonates, amine complexes, ammonium salts and/or hydroxides of metals present in the active composition.

Preferably, the intimate dry mixture is produced by intimately mixing the sources. The intimate mixing can be effected in dry or wet form. If it is effected in dry form, the sources are appropriately used in the form of finely divided powders. Particularly intimate dry mixtures are obtained in the course of mixing when the starting materials are exclusively sources present in dissolved form. Therefore, the intimate mixing of the sources is preferably effected in wet form. Preferably, the sources are mixed with one another in the form of solutions and/or suspensions and the resulting wet mixture is subsequently dried to give the intimate dry mixture. The solvents and/or suspension media used are preferably water or an aqueous solution. The wet mixture is preferably dried by spray-drying with exit temperatures of 100 to 150° C. The drying gas stream is preferably air or molecular nitrogen.

Before the calcination, the dry mixture (for example a dry mixture obtained by spray-drying) can be subjected to a material processing operation by mixing. The term "mixing" is understood to mean dry mixing, kneading and stirring, optionally with addition of liquid. The mixing gives a homogenized composition with relatively narrow particle size distribution.

Particularly advantageously, the mixing operation is performed after addition of a liquid, for example of water, acetic acid or the like, as a kneading operation, wherein a ductile or plasticized material is obtained. The shear forces which act therein comminute agglomerates. The ductile material is suitable for extrusion and gives stable extrudates which can be dried. The dried extrudates are advantageously suitable, inter alia, for calcination in a rotary tube.

The calcination can be performed either under inert gas or under an oxidative atmosphere, or else under a reducing atmosphere. Preferably, the calcination is performed under an oxidative atmosphere. Useful inert gases are especially nitrogen, water vapor, noble gases, and mixtures thereof. The oxidative atmosphere preferably comprises oxygen, especially air. The reducing atmosphere comprises preferably $H_2$, $NH_3$, CO, methane and/or acrolein. The catalytic activity of the active composition generally exhibits an optimum depending on the oxygen content of the calcination atmosphere. Preferably, the oxygen content of the calcination atmosphere is 0.5 to 10% by volume, more preferably 1 to 5% by volume. Oxygen contents above and below the aforementioned limits normally reduce the resulting catalytic activity. The calcination time may be a few minutes to a few hours and typically decreases with the level of the calcination temperature. A calcination process of good suitability is described, for example, by WO 95/11081.

The calcining of the dry mixture gives the active composition. The conversion to powder form is preferably effected by grinding.

In an alternative process for preparing the catalyst, finely divided precursor composition is first applied to the surface of the shaped support body and the calcination of the precursor composition to the active composition on the surface of the shaped support body is performed. The finely divided precursor composition preferably comprises sources of the elemental constituents of the active composition. The active composition is preferably an active composition of the general formula (I) or (II).

In a process according to the invention for preparing the catalyst, the shaped support body is coated with the active composition by mixing a multitude of shaped support bodies, a pulverulent active composition and a liquid binder, without saturating the pulverulent active composition with the liquid binder, in a vessel, the duration of the coating operation being less than 30 minutes. The saturation of the pulverulent active composition with the liquid binder is avoided by selecting the ratio of the amount of liquid binder to the amount of pulverulent active composition such that the amount of binder remains below the liquid absorption capacity of the pulverulent active composition.

The liquid absorption capacity of powders can be determined, for example, by stirring up the powder in a stirrer and applying liquid to the stirred powder and measuring the torque at the stirrer motor against time. The amount of liquid which has been applied to the powder up to the maximum torque can be used to calculate the liquid absorption capacity of the powder.

The pulverulent active composition preferably has a proportion of particles having a longest dimension above 50 µm of less than 1%.

The term "binder" is understood to mean substances which permanently or temporarily improve the adhesion of the active composition powder particles to one another and/or to the support material. Preferably, the binder essentially vaporizes or sublimes in the course of subsequent drying. In the process according to the invention, the binders used may, for example, be polyols such as ethylene glycol, propylene glycol, butylene glycols, glycerol, or amides such as formamide, N,N-dimethylformamide, N,N-diethylformamide, N,N-dibutylformamide, acetamide, pyrrolidone or N-methylpyrrolidone. The liquid binder is preferably selected from water, glycerol and solutions of glycerol in water. A preferred liquid binder is a solution of glycerol in water comprising 20 to 99% by weight of water. A particularly preferred liquid binder is a solution of glycerol in water comprising 75% by weight of water.

Preferably, the shaped support bodies are initially charged in the vessel, and the pulverulent active composition and the liquid binder are added separately to the vessel over the duration of the coating. Thus, the pulverulent active composition and the liquid binder are only contacted with one another in the vessel. The pulverulent active composition and the liquid binder are preferably combined only on the surface of the shaped support bodies initially charged in the vessel. This is achieved by spraying the liquid binder into the vessel and introducing the pulverulent active composition into a region of the vessel outside the spray cone of the liquid binder. Thus, local overloading of the powder particles with liquid is avoided. The pulverulent active composition and the liquid binder can be introduced into the vessel over the duration of the treatment, for example, by continuous addition or by separate addition of portions over time.

The mixing is preferably effected by continuous movement of the vessel. The movement is preferably a rotational movement.

The process principle disclosed in DE-A 2909671 (cf. also EP-A 714 700 and DE-A 10 2005 010 645) using the liquid binder desired in each case is particularly suitable for performance of the above-described process for preparing the catalyst.

In other words, the shaped support bodies to be coated, preferably hollow cylindrical shaped support bodies, are introduced into a preferably inclined (the angle of inclination is generally 30 to 90°) rotating vessel (for example rotary pan or coating tank or coating drum). Suitable rotary vessels for this end use are especially the Hi-Coater HCF-100 from Freund Industrial Co., Ltd, Tokyo (JP), and the Hi-Coater LH 100 from Gebrüder Lödige Maschinenbau GmbH, Paderborn, Germany.

The rotating vessel conducts the shaped support bodies, preferably the hollow cylindrical shaped support bodies, under two metering apparatuses arranged in succession at an advantageous separation. The first of the two metering devices appropriately corresponds to a nozzle, by which the shaped support bodies rolling within the rotating pan (Hi-Coater) are moistened in a controlled manner with the liquid binder. Appropriately in application terms, the second metering apparatus is outside the atomization cone of the liquid binder sprayed in, and serves to supply the pulverulent active composition (for example via a shaking channel). The shaped support bodies take up the active composition, since the active composition is compacted to a coherent shell on the surface of the shaped support bodies through the rolling motion.

If required, the thus base-coated, preferably hollow cylindrical shaped support body, in the course of the subsequent rotation, again passes through the spray nozzle, is moistened in a controlled manner (optionally with another liquid binder), in order to be able to take up a further layer (optionally another layer) of pulverulent active composition in the course of further movement etc. (intermediate drying is generally not required). The at least partial removal of the liquid binder used can, for example, following the teaching of EP-A 714 700 or the teaching of DE-A 10 2005 010 645, be effected by final supply of heat, for example through the action of hot gases such as $N_2$ or air (these are fed in and removed through spatially separated wall elements configured like a grid in the rotary pan, or coating tank, or coating drum (rotary vessel in general)).

It is of significance for the embodiment of the coating process described that the moistening of the surface of the shaped support bodies to be coated is undertaken in a controlled manner. In short, this means that the support surface is appropriately moistened in such a way that it has adsorbed liquid binder but this is not visually apparent on the support surface. If the shaped support body surface is too moist, the finely divided active composition and/or precursor composition agglomerates to give separate agglomerates, rather than adhering to the surface. More detailed information in this regard can be found in DE-A 2909671, in EP-A 714 700 and in DE-A 10 2005 010 645. One benefit of the procedure described is that the removal of the liquid binder used can be undertaken in a comparatively controlled manner, for example through evaporation and/or sublimation. In the simplest case, this can be effected, as already explained, through the action of hot gases at appropriate temperature (frequently 50 to 150° C.). Such an action of hot gases generally causes preliminary drying.

The removal of the binder can be effected within a drying apparatus of any kind (for example in a belt dryer) and/or not until within the fixed catalyst bed of the shell and tube reactor, as recommended, for example, by DE-A 10 2005 010 645. Preferably, the inventive catalyst is obtained by removing the liquid binder from the coated shaped support body by drying at a temperature in the range from 150 to 400° C., preferably 250 to 350° C. The drying is preferably conducted in an air stream. Preferably, the duration of drying is 0.5 to 8 h, preferably 1 to 4 h.

The invention also provides a process for preparing an $\alpha,\beta$-unsaturated carboxylic acid by gas phase oxidation of an $\alpha,\beta$-unsaturated aldehyde with molecular oxygen over a fixed catalyst bed, wherein the fixed catalyst bed comprises a bed of an inventive catalyst. Preferably, the molecular oxygen and the $\alpha,\beta$-unsaturated aldehyde are contacted with the fixed catalyst bed by conducting the molecular oxygen and the $\alpha,\beta$-unsaturated aldehyde over the fixed catalyst bed. Preferably, a reaction gas comprising the molecular oxygen and the $\alpha,\beta$-unsaturated aldehyde is conducted over the fixed catalyst bed and the reaction gas is thus converted to a product gas.

The $\alpha,\beta$-unsaturated aldehyde is preferably selected from $\alpha,\beta$-unsaturated aldehydes comprising 3 to 6 (i.e. 3, 4, 5 or 6) carbon atoms, especially from acrolein and methacrolein. More preferably, the $\alpha,\beta$-unsaturated aldehyde is acrolein. The process is particularly suitable for preparation of $\alpha,\beta$-unsaturated carboxylic acids, especially for oxidation of acrolein to acrylic acid and of methacrolein to methacrylic acid. It is preferably a process for preparing acrylic acid by gas phase oxidation of acrolein.

The molecular oxygen is preferably supplied to the process in the form of air.

The proportion of the $\alpha,\beta$-unsaturated aldehyde present in the reaction gas will generally be 3 to 15% by volume, preferably 4 to 10% by volume, more preferably 5 to 8% by volume, based in each case on the reaction gas.

Preferably, the reaction gas also comprises at least one inert diluent gas other than water vapor. This is understood to mean those gases which, in the course of the gas phase oxidation, remain chemically unchanged to an extent of at least 95 mol %, preferably to an extent of at least 98 mol %. Examples of inert diluent gases are $N_2$, $CO_2$ and noble gases such as Ar. The inert diluent gas used is preferably molecular nitrogen. The inert diluent gas may comprise at least 20% by volume, preferably at least 40% by volume, further preferably at least 60% by volume, more preferably at least 80% by volume, most preferably at least 95% by volume, of molecular nitrogen.

The reaction gas may also comprise water vapor.

The reaction gas may also comprise cycle gas. Cycle gas is understood to mean the residual gas which remains when $\alpha,\beta$-unsaturated carboxylic acid is essentially selectively separated from the product gas of the gas phase oxidation.

Preferably, the process according to the invention for preparing the $\alpha,\beta$-unsaturated carboxylic acid forms the second stage of a two-stage gas phase oxidation of an alkene to the $\alpha,\beta$-unsaturated carboxylic acid. In the course of such a two-stage gas phase oxidation, the product gas of the first stage is preferably supplied to the second stage. Before being supplied to the second stage, the product gas from the first stage can, for example, be cooled and/or oxygen can be added (secondary addition of oxygen, preference being given to the addition of air). The cycle gas is preferably conducted into the first of the two stages.

In the reaction gas, the molar ratio of $O_2$:$\alpha,\beta$-unsaturated aldehyde is preferably in the range from 1 to 3, preferably in the range from 1 to 2, more preferably in the range from 1 to 1.5.

The reaction gas preferably comprises $\alpha,\beta$-unsaturated aldehyde:oxygen:water vapor:inert diluent gas other than water vapor in a volume ratio of 1:(1 to 3):(0 to 20):(3 to 30), preferably of 1:(1 to 3):(0.5 to 10):(7 to 10).

Preferably, the space velocity of $\alpha,\beta$-unsaturated aldehyde on the bed is not more than 600 l (STP)/(lh), preferably not more than 300 l (STP)/(lh), more preferably not more than 250 l (STP)/(lh), most preferably not more than 200 l (STP)/(lh). Preferably, the space velocity of $\alpha,\beta$-unsaturated aldehyde on the bed is at least 30 l (STP)/(lh), preferably at least 70 l (STP)/(lh), more preferably at least 90 l (STP)/(lh), most preferably at least 120 l (STP)/(lh). The space velocity of $\alpha,\beta$-unsaturated aldehyde on the bed expressed in l (STP)/(lh) is understood to mean the amount of $\alpha,\beta$-unsaturated aldehyde in standard liters which is conducted over the fixed catalyst bed as a constituent of the reaction gas per hour per liter of bed. One standard liter (l (STP)) is the volume in liters that the molar amount of an ideal gas corresponding to the molar amount of $\alpha,\beta$-unsaturated aldehyde would occupy under standard conditions, i.e. at 25° C. and 1 bar.

In general, a total pressure of 0.5 to 100 bar, preferably of 1 to 5 bar, especially of 1 to 3 bar, exists in the reaction gas. All pressure figures in this document relate to absolute pressures.

Preferably, the process for preparing the $\alpha,\beta$-unsaturated carboxylic acid is performed in a shell and tube reactor, the reaction tubes of which have been filled with the fixed catalyst bed.

The bed may, for example, consist exclusively of inventive catalysts. It is also possible for substantially homogeneous mixtures of inventive catalysts and shaped diluent bodies which are essentially inert with respect to the gas phase oxidation to be present in the bed. Useful materials for the shaped diluent bodies include, for example, porous or nonporous aluminum oxides, silicon dioxide, zirconium dioxide, silicon carbide, silicates such as magnesium silicate or aluminum silicate and/or steatite (for example of the C220 type from CeramTec, Germany).

The geometry of the shaped diluent bodies may in principle be as desired. In other words, they may, for example, be rings, spheres, tablets, punched tablets, trilobes, punched trilobes, star extrudates, star tablets, wagonwheels, extrudates, pills, cylinders and hollow cylinders.

The shell and tube reactor is preferably a two-zone shell and tube reactor. A preferred two-zone shell and tube reactor is disclosed by DE-C 28 30 765. But the two-zone shell and tube reactors disclosed in DE-C 25 13 405, U.S. Pat. No. 3,147,084, DE-A 22 01 528, EP-A 383224 and DE-A 29 03 582 are also suitable.

In the two-zone shell and tube reactor, two essentially spatially separate temperature control media are preferably conducted around the reaction tubes. The temperature control media are preferably salt melts. The entrance temperature of the temperature control medium is preferably set to 230 to 300° C., preferably to 240 to 290° C., more preferably to 250 to 285° C. The temperature control medium can be conducted in cocurrent or in countercurrent to the reaction gas mixture through the respective temperature control zone. Within the temperature control zone, the temperature control medium is preferably conducted in a meandering manner. The flow rate of the temperature control medium within the respective temperature control zone is preferably selected such that the temperature of the heat exchange medium from the inlet site into the temperature zone to the outlet site from the temperature zone rises by 0 to 15° C., frequently 1 to 10° C., or 2 to 8° C., or 3 to 6° C.

In a preferred embodiment, the fixed catalyst bed comprises at least two successive reaction zones, in which case the bed, at least in the reaction zone that is most closely to the reactor inlet, comprises an inventive catalyst.

In another preferred embodiment, the fixed catalyst bed comprises at least two successive reaction zones, in which case the bed, at least in the reaction zone in which the highest local temperature occurs, comprises an inventive catalyst.

The individual reaction zones differ from one another in at least one property selected from the content of inert shaped diluent bodies, shape of the catalysts, degree of space filling by the catalysts, active composition content of the catalysts and chemical composition of the active material.

As a result of the different properties, the volume-specific catalyst activity of one reaction zone may differ from the volume-specific catalyst activity of another reaction zone. Preferably, the volume-specific catalyst activity increases from one reaction zone to the next from the reactor inlet to the reactor outlet.

The (relative) volume-specific catalyst activity can be determined as the reaction rate, based on the catalyst bed volume, under otherwise constant conditions.

The volume-specific catalyst activity can be varied through dilution of the catalyst with shaped diluent bodies. Alternatively or additionally, the volume-specific catalyst activity can be adjusted by varying the active composition content.

Preferably, the spatial active composition density, i.e. the amount of active composition in g per unit spatial volume of the reaction zone in liters, is lower in the reaction zone closest to the reactor inlet than in the reaction zone closest to the reactor outlet.

From a certain operating time, increasing duration of operation is accompanied by an increasing reduction in the quality of the catalyst charge. In a preferred embodiment, to restore the quality of the bed, not the entire spent bed but only the portion of the bed in which the highest local temperature occurs is removed and replaced by a fresh bed. For example, the bed in that reaction zone in which the highest local temperature occurs is replaced by a fresh bed, and the bed is retained in the reaction zones downstream in flow direction of the reaction gas.

In general, the shell and tube reactor additionally has thermal tubes to determine the gas temperature in the catalyst bed. Appropriately, the internal diameter of the thermal tubes and the diameter of the accommodating sleeve within for the thermocouple is selected such that the ratio of volume which evolves heat of reaction to heat-removing surface area is the same or only slightly different in thermal tubes and reaction tubes.

The pressure drop should be the same in reaction tubes and thermal tubes, based on the same GHSV. Any pressure drop in the thermal tube can be balanced out, for example, by adding spalled catalyst to the catalysts. This balancing is appropriately homogeneous over the entire thermal tube length. For the rest, the filling of thermal tubes may be configured as described in EP-A 873783.

The temperatures measured in the thermal tubes can be used to determine the highest local temperature of the fixed catalyst bed and the position thereof in the fixed catalyst bed.

FIGURES

FIG. 1a shows the cumulative particle size distribution of the finely divided powder P. The abscissa shows the particle diameter in μm on a logarithmic scale. The ordinate value on the distribution curve corresponding to a particular particle diameter shows the percentage of the total particle volume which consists of particles of the particular particle diameter or of a smaller particle diameter.

FIG. 1b shows the differential particle size distribution of the finely divided powder P. The abscissa shows the particle diameter in μm on a logarithmic scale. The ordinate value on the distribution curve corresponding to a particular particle diameter shows the percentage of the total particle volume which consists of particles of the particular particle diameter.

Figure 1A:
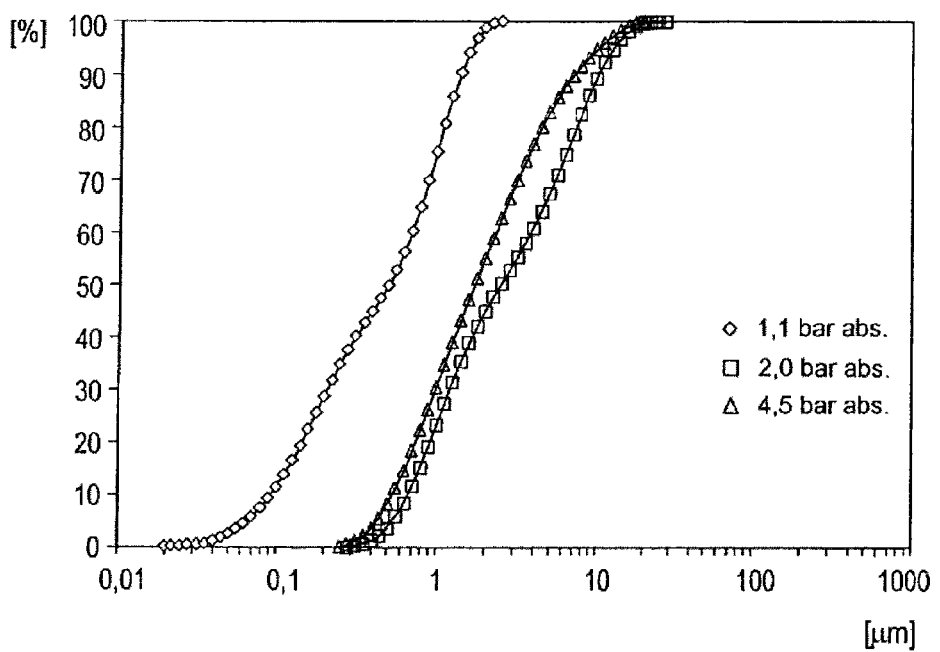

In FIGS. 3 to 13, the particular pore diameter in μm is plotted on the abscissa (logarithmic plot to base 10). Plotted on the ordinate in (ml/g of active composition) is the integral over the individual contributions of the individual pore diameters to the specific total pore volume (the cumulative contribution to the specific total pore volume) (□ curve). The end point is the (specific) total pore volume based on the active composition (total intrusion volume).

EXAMPLES

Preparation of Catalysts

A) Preparation of a Precursor Composition

In a water-heated 1.75 $m^3$ jacketed stainless steel vessel having a beam stirrer, 8.2 kg of copper acetate hydrate (content: 32.0% by weight of Cu, addition rate 50 kg/h, from Goldschmidt) were dissolved in 274 l of water at room temperature (−25° C.) while stirring (speed: 70 revolutions/min). A solution 1 was obtained. This was stirred for a further 30 min.

Spatially separately from this, a water-heated 1.75 m³ jacketed stainless steel vessel having a beam stirrer (speed: 70 revolutions/min) was initially charged with 614 l of water and heated to 40° C., and 73 kg of ammonium heptamolybdate tetrahydrate (81.5% by weight of $MoO_3$, addition rate 300 kg/h, from H.C. Starck GmbH) were stirred in while maintaining the 40° C. Then the vessel contents were heated to 90° C. within 30 min while stirring and, while maintaining this temperature, the following were stirred in successively and in the sequence mentioned: 12.1 kg of ammonium metavanadate (77.6% of $V_2O_5$, addition rate 150 kg/h, further stirring time after addition 40 min) and 10.7 kg of ammonium paratungstate heptahydrate (89.6% by weight of $WO_3$, addition rate 50 kg/h, further stirring time after addition 30 min). A solution 2 was obtained.

Solution 2 was cooled to 80° C. and then solution 1 was transferred into solution 2 rapidly at a stirrer speed of the beam stirrer of 70 revolutions/min, and stirred in. The mixture obtained was admixed with 133 l of a 25% by weight aqueous $NH_3$ solution at a temperature of 25° C. While stirring, a clear solution formed, which briefly had a temperature of 65° C. and a pH of 8.5. It was drained into a further water-heated 1.75 m³ jacketed stainless steel vessel having a beam stirrer. The vessel contents were heated to 80° C., stirred at a stirrer speed of 40 revolutions/min and circulated. The pH of the vessel contents was kept at a value of 8.5 by means of automatic addition of a 25% by weight aqueous $NH_3$ solution. The vessel contents were pumped into the rotary disk spray tower of the FS 15 type from Niro (Denmark) and dried in a hot air cocurrent at a gas inlet temperature of 350±10° C., a disk speed of 15 000 rpm and a combustion air volume flow rate of 2300 m³ (STP/h), while maintaining a reduced pressure of 1 mbar in the spray tower. The liquid volume flow rate metered into the spray tower was regulated such that a gas outlet temperature of 110±5° C. was attained. The resulting spray powder had a particle diameter of 2 to 50 μm and an ignition loss of 21±2% by weight. The ignition loss was determined by heating in a porcelain crucible (3 h at 600° C.) under air. The porcelain crucible had been calcined at 900° C. to constant weight beforehand. The spray powder was dispensed into special containers or special vats (200 liters) with a plastic inlet. To remove all lumps, a sieve insert was used.

75 kg of spray powder thus obtained were metered into a kneader from AMK (Aachener Misch- and Knetmaschinen Fabrik) of the VM 160 type (Sigma blades) at a screw speed of 15 revolutions/min. Subsequently, 6.5 l of acetic acid (100% by weight, glacial acetic acid) and 5.2 l of water were metered into the kneader at a screw speed of 15 revolutions/min. After a kneading time of 4 to 5 minutes (speed of the screw: 20 revolutions/min), a further 6.5 l of water were added and the kneading operation was continued until 30 minutes had passed (kneading temperature about 40 to 50° C.). In the course of kneading, the power consumption was observed. On exceedance of a power consumption of 25%, about another 1 l of water were added to the kneading material if required. Thereafter, the kneading material was emptied into an extruder and shaped by means of the extruder (from Bonnot Company (Ohio), type: G 103-10/D7A-572K (6" Extruder W Packer) to give extrudates (length: 1-10 cm; diameter 6 mm). In a 3-zone belt dryer, the extrudates were dried at a belt speed of 10 cm/min and a resulting residence time of 64 min and a gas inlet temperature of 155° C. The expected values for the gas temperatures are 90-95° C. in zone 1, about 115° C. in zone 2 and about 125° C. in zone 3.

B) Preparation of an Active Composition of the Formula $Mo_{12}V_3W_{1.2}Cu_{1.2}O_n$ The thermal treatment was performed in the rotary tube oven described in DE 10360057A1, under the following conditions:
the thermal treatment was effected batchwise with a material amount of 306 kg, which
had been prepared as described under A);
the angle of inclination of the rotary tube to the horizontal was≈0°;
the rotary tube rotated to the right at 1.5 revolutions/min;
over the course of the entire thermal treatment, a gas stream of 205 m³ (STP)/h was conducted through the rotary tube, which (after displacement of the air originally present) had the following composition and was supplemented at the outlet thereof from the rotary tube by a further 25 m³ (STP)/h of barrier gas nitrogen: 80 m³ (STP)/h composed of baseload nitrogen and gases released in the rotary tube, 25 m³ (STP)/h of barrier gas nitrogen, 30 m³ (STP)/h of air and 70 m³ (STP)/h of recirculated cycle gas. The barrier gas nitrogen was supplied at a temperature of 25° C. The mixture of the other gas streams, coming from the heater, was in each case conducted into the rotary tube at the temperature that each material had in the rotary tube.

Within 10 h, the material temperature was raised from 25° C. in an essentially linear manner to 300° C.; then the material temperature was raised in an essentially linear manner to 360° C. within 2 h; subsequently, the material temperature was lowered in an essentially linear manner to 350° C. within 7 h; then the material temperature was increased in an essentially linear manner to 420° C. within 2 h and this material temperature was maintained for 30 min; then the 30 m³ (STP)/h of air in the gas stream conducted through the rotary tube were replaced by a corresponding increase in the baseload nitrogen (which ended the operation of the actual thermal treatment), the heating of the rotary tube was switched off and the material was cooled to a temperature below 100° C. by switching on the rapid cooling of the rotary tube by inward suction of ambient air within 2 h, and finally to room temperature; the gas stream was fed to the rotary tube here at a temperature of 25° C.; over the entire thermal treatment, the pressure (immediately) beyond the rotary tube outlet of the gas stream was 0.2 mbar below the external pressure.

The oxygen content of the gas atmosphere in the rotary tube oven in all phases of the thermal treatment was 2.9% by volume. Over the total duration of the reductive thermal treatment, on arithmetic average, the ammonia concentration of the gas atmosphere in the rotary tube oven was 4% by volume.

The catalytically active material obtained was ground by means of a biplex crossflow classifying mill (BQ 500) (from Hosokawa-Alpine Augsburg) to give a finely divided powder P. 24 long blades were installed here into the milling tracks. The milling speed was 2500 revolutions/min. The ventilator throttle flap was fully open. The dosage was set to 2.5 revolutions/min. The air output volume flow rate was 1300 m³/h, the pressure differential 10-20 mbar. 50% of the powder particles of the finely divided powder resulting from the grinding passed through a sieve of mesh size 1 to 10 μm. The proportion of particles having a longest dimension above 50 μm in the finely divided powder was less than 1%. The size distribution of the particles of the above ground catalytically active multielement oxide composition powder is shown in FIGS. 1a and 1b as a function of the dispersion pressure of the compressed air used for dry dispersion (◇=1.1 bar abs.; □=2.0 bar abs.; ∆=4.5 bar abs.).

Figure 1B:
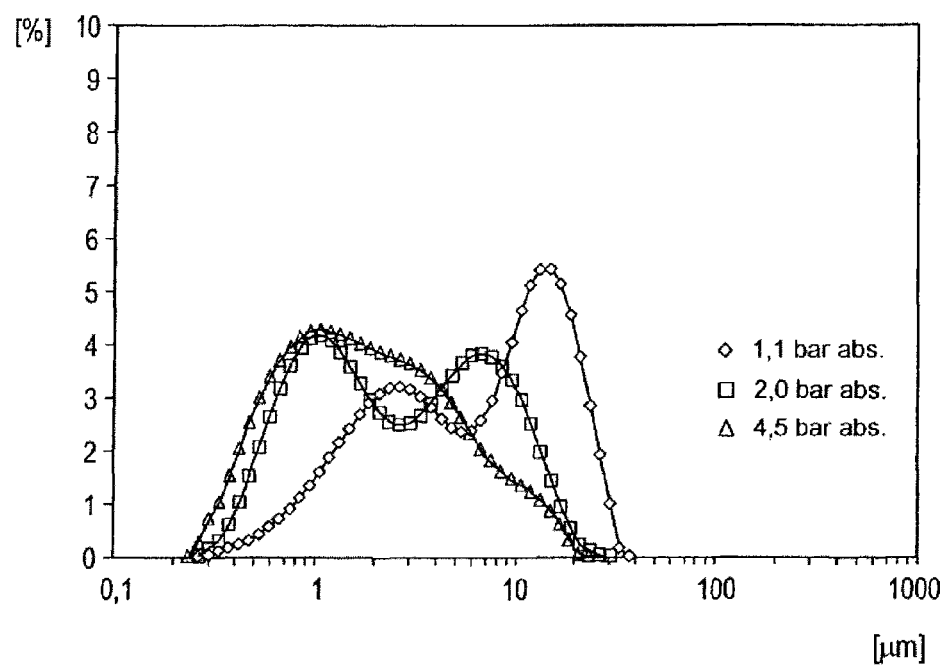

The measurement method underlying the particle diameter distribution of FIGS. 1a and 1b is laser diffraction. This involved conducting the multielement oxide composition powder through a dispersing channel into the Sympatec RODOS dry disperser (Sympatec GmbH, System-Partikel-Technik, Am Pulverhaus 1, D-38678 Clausthal-Zellerfeld), dry-dispersing it therein with compressed air (which had the respective dispersing pressure of 1.1 or 2 or 4.5 bar abs.) and blowing it to the measurement cell in a free jet. Then, according to ISO 13320, the Malvern Mastersizer S laser diffraction spectrometer (Malvern Instruments, Worcestershire WR14 1AT, United Kingdom) was used to determine the volume-based particle diameter distribution therein (obscuration 3-7%).

Figure 2:
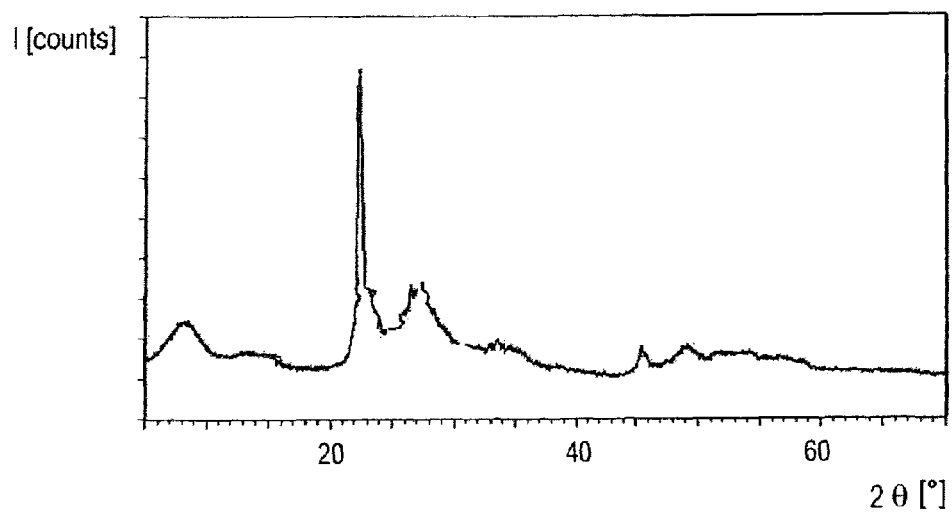
FIG. 2 shows a diffractogram of the finely divided powder P.

FIG. 2 shows the X-ray diffractogram of the finely divided powder P. The abscissa shows the diffraction angle on the 2Θ scale [degrees]. Plotted on the ordinate is the absolute intensity.

C) Shaping of the Active Composition

C1 (Comparative Example)

1600 g of hollow cylindrical support bodies (external diameter 7 mm, length 3 mm, internal diameter 4 mm, C220 steatite from CeramTec having a surface roughness $R_Z$ of 45 μm (grit layer)) were coated with the ground finely divided powder P. The coating was effected in a HiCoater LHC 25/36 (from Lödige, D-33102 Paderborn). This HiCoater had been modified in order to enable continuous powder metering. This consisted of a funnel-shaped powder reservoir, which was connected via a Tygon hose (internal diameter: 8 mm, external diameter 11.1 mm; from Saint-Gobain Performance, 89120 Charny, France) to the drum of the HiCoater. The drum radius was 18 cm. The depth of the drum is 20 cm. The axis about which the drum rotated was aligned horizontally. For the coating, 750 g of the ground catalytically active oxide composition powder were introduced into the powder reservoir. The powder was metered in by continuous pressure metering. The pulse-timed valve was set to 50 ms and the pressure set was 0.7 bar above ambient pressure (~1 atm). The powder in the funnel-shaped powder reservoir was stirred continuously during the coating in order to ensure homogeneous metering (stirrer run time: 2 s, stirrer pause time: 1 s, modified V-shaped anchor stirrer, built in-house at BASF SE). The binder was an aqueous solution of 75% by weight of water and 25% by weight of glycerol. This was sprayed into the drum separately via a liquid metering device. The liquid was pumped with a Watson-Marlow HPLC pump (323 type) into the metering arm, which is within the drum (spray pressure 3 bar, forming pressure 2 bar, flow rate: 3 g of glycerol/water solution (1:3)/min). The powder metering and liquid metering devices are arranged parallel to one another. The nozzle from Schlick (DE) of the 570/0 S75 type, mounted on the metering arm, and the exit orifice of the solid metering device likewise secured below on the metering arm were aligned in parallel at a distance of 6 cm and, with the aid of an angle-measuring instrument, at an angle of 40° to the horizontal. The powder is metered in outside the spray cone of the nozzle. The nozzle orifice and exit orifice of the solid metering device show a direction of rotation of the drum. The drum rotated clockwise at 15 rpm during the coating. The coating was effected at 25° C. over a period of 50 min. Thereafter, the coated support materials were dried at air input temperature 130° C. and air output temperature 81° C. for 27 min. Thereafter, they were cooled to 25° C. in the drum at rest over a period of 30 min. During the coating, the powder supplied was for the most part taken up on the surface of the support. The portions which were not taken up were collected in a filter downstream of the drum. There was no formation of pairs, and no agglomeration of the finely divided oxidic composition was observed.

The coated shaped support bodies were treated in an air circulation drying cabinet from Memmert GmbH+Co. KG (UM 400 type; internal volume=53 l; air flow rate=800 l/h), in order to remove the glycerol still present in the sample. For this purpose, the air circulation drying cabinet was heated to 300° C. (including the air temperature) within 2 h and then kept at 300° C. for 2 h. During the drying, the drying material was layered on a perforated sheet positioned in the center of the drying cabinet (the hole diameter of the passage orifices distributed homogeneously over the perforated sheet=0.5 cm; the orifice ratio of the perforated sheet was 60%; the total cross-sectional area of the perforated sheet was 35 cm×26 cm=910 cm$^2$) (bed height=2 cm). Thereafter, the air circulation drying cabinet was cooled to 40 to 50° C. within 2 to 3 h and the sample was removed. The hollow cylindrical eggshell catalysts C1 removed from the air circulation drying cabinet had, based on the total mass thereof, an oxidic eggshell content of 29.1% by weight.

C2 (Comparative Example)

335 kg of the ground finely divided powder P were mixed vigorously with 50 kg of molybdenum trioxide from Climax (66.6% by weight of Mo, the $MoO_3$ fulfills all the requirements listed in DE 10 2007 010 422 A1) in an R645 mixer from AMK in Aachen (DE) for a mixing time of 10 min. This was an inclined mixer with cutting blades (intensive mixer). The mixing arm rotates at 39 revolutions/min. The resulting powder is referred to hereinafter as PMo powder.

The shaping was then effected as follows: 61 kg of hollow cylindrical support bodies (external diameter 7 mm, length 3 mm, internal diameter 4 mm; steatite of the C220 type from Ceram Tec having a surface roughness $R_Z$ of 45 μm and a total pore volume based on the volume of the support body of 1% by volume; cf. DE-A 2135620) were introduced into a coating tank (angle of inclination 90°; Hicoater from Lödige, DE) of capacity 200 l. Subsequently, the coating tank was set in rotation at 16 rpm. Via a nozzle of the Schlick 0.5 mm, 90° type, 3.8 to 4.2 liters of an aqueous solution of 75% by weight water and 25% by weight of glycerol were sprayed onto the support bodies at a liquid supply pressure of about 1.8 bar within 40 min. At the same time, within the same period, 18.3 kg of the PMo powder were metered in continuously via a shaking channel outside the spray cone of the atomizer nozzle. During the coating, the powder supplied was taken up completely onto the surface of the support body; no agglomeration of the finely divided oxidic active composition or pair formation was observed.

After the addition of active composition powder and aqueous solution had ended, air (about 400 m$^3$/h) at 110° C. (alternatively 80 to 120° C.) was blown into the coating tank at a rotational speed of 2 rpm for 40 min (alternatively 15 to 60 min).

A sample of about 2 kg of coated active composition powder was taken. The glycerol still present in the sample was removed in the air circulation drying cabinet from Memmert GmbH+Co. KG (UM 400 type; capacity=53 l; air flow rate=800 l/h). The heat treatment conditions were identical to those of example C1. The hollow cylindrical eggshell catalysts C2 removed from the air circulation drying cabinet had, based on the total mass thereof, an oxidic eggshell content of 22% by weight.

C3 (Comparative Example)

The shaping was then effected as follows: 70 kg of hollow cylindrical support bodies (external diameter 7 mm, length 3 mm, internal diameter 4 mm; steatite of the C220 type from CeramTec having a surface roughness $R_Z$ of 45 μm and a total pore volume based on the volume of the support body of ≤1% by volume; cf. DE-A 2135620) were introduced into a coating tank (angle of inclination 90°; Hicoater from Lödige, DE) of capacity 200 l. Subsequently, the coating tank was set in rotation at 16 rpm. Via a nozzle of the Schlick 0.5 mm, 90° type, 3.8 to 4.2 liters of an aqueous solution of 75% by weight of water and 25% by weight of glycerol were sprayed onto the support bodies at a liquid supply pressure of about 1.8 bar within 40 min. At the same time, within the same period, 18.2 kg of the ground finely divided powder P (the specific surface area of which was 16 m$^2$/g) were metered in continuously via a shaking channel outside the spray cone of the atomizer nozzle. During the coating, the powder supplied was taken up completely onto the surface of the support body; no agglomeration of the finely divided oxidic active composition or pair formation was observed.

After the addition of active composition powder and water had ended, air (about 400 m$^3$/h) at 110° C. (alternatively 80 to 120° C.) was blown into the coating tank at a rotational speed of 2 rpm for 40 min (alternatively 15 to 60 min). Hollow cylindrical eggshell catalysts were obtained, in which the proportion of oxidic active composition, based on the overall composition, was 20% by weight.

A sample of about 2 kg of coated active composition powder was taken. The glycerol still present in the sample was removed in an air circulation drying cabinet from Memmert GmbH+Co. KG (UM 400 type; capacity=53 l; air flow rate=800 l/h). The heat treatment conditions were identical to those of example C1. The hollow cylindrical eggshell catalysts C3 removed from the air circulation drying cabinet had, based on the total mass thereof, an oxidic eggshell content of 20% by weight.

C4 (Comparative Example)

The shaping of catalyst C4 was effected as for C1, except that, in contrast to C1, only 600 g of powder were introduced into the powder reservoir and the coating was effected over a period of 40 min. After the heat treatment in the air circulation drying cabinet, conducted as in C1, the hollow cylindrical eggshell catalysts C4 removed from the air circulation drying cabinet, based on the total mass thereof, had an oxidic eggshell content of 20.0% by weight.

C5 (Comparative Example)

The coating was effected in a rotating coating drum (internal diameter=25.5 cm; 36 rpm) with a granulating system from ERWEKA (DE). The axis of rotation of the drum was set at an angle of 51.6° in relation to the horizontal. The coating drum was filled with 800 g of hollow cylindrical support bodies (external diameter 7 mm, length 3 mm, internal diameter 4 mm, C220 steatite from CeramTec having a surface roughness $R_Z$ of 45 μm (grit layer)). The binder used was an aqueous solution of 75% by weight of water and 25% by weight of glycerol. About 76 g of the liquid binder were sprayed onto the support bodies via a nozzle (nozzle diameter=1 mm) within the coating time of 45 min. At the same time, within the same period, 200 g of ground finely divided powder P was metered in continuously by means of a conveying screw outside the spray cone of the atomizer nozzle. During the coating, the powder supplied was taken up completely onto the surface of the support bodies. No agglomeration of the finely divided oxidic active composition was observed. The coating operation was repeated. The total amount from the two coating experiments was combined to one sample. The sample was treated in an air circulation drying cabinet from Memmert GmbH+Co. KG (UM 400 type; capacity=53 l; air flow rate=800 l/h), in order to remove the glycerol still present in the sample. The heat treatment conditions were identical to those of example C1. The hollow cylindrical eggshell catalysts C5 removed from the air circulation drying cabinet had, based on the total mass thereof, an oxidic eggshell content of 19.6% by weight.

C6 (Example)

The shaping of catalyst C6 was effected as for C1, except that, in contrast to C1, only 451 g of powder were introduced into the powder reservoir and the coating was effected over a period of 30 min. After the heat treatment in the air circulation drying cabinet, conducted as in C1, the hollow cylindrical eggshell catalysts C6 removed from the air circulation drying cabinet, based on the total mass thereof, had an oxidic eggshell content of 18.0% by weight.

C7 (Example)

The shaping of catalyst C7 was effected as for C1, except that, in contrast to C1, only 377.5 g of powder were introduced into the powder reservoir and the coating was effected over a period of 25 min. After the heat treatment in the air circulation drying cabinet, conducted as in C1, the hollow cylindrical eggshell catalysts C7 removed from the air circulation drying cabinet, based on the total mass thereof, had an oxidic eggshell content of 15.8% by weight.

C8 (Example)

The shaping of catalyst-C8 was effected as for C5, except that, in contrast to C5, only about 44 g of the liquid binder were sprayed onto the support bodies via a nozzle (nozzle diameter=1 mm) and the coating was effected within 27.5 min. After the heat treatment in the air circulation drying cabinet, conducted as in C1, the hollow cylindrical eggshell catalysts C8 removed from the air circulation drying cabinet, based on the total mass thereof, had an oxidic eggshell content of 15.5% by weight.

C9 (Example)

The shaping of catalyst C9 was effected as for C5, except that, in contrast to C5, only about 29 g of the liquid binder were sprayed onto the support bodies via a nozzle (nozzle diameter=1 mm) and the coating was effected within 16 min. After the heat treatment in the air circulation drying cabinet, conducted as in C1, the hollow cylindrical eggshell catalysts C9 removed from the air circulation drying cabinet, based on the total mass thereof, had an oxidic eggshell content of 10.8% by weight.

C10 (Example)

The shaping of catalyst C10 was effected as for C1, except that, in contrast to C1, only 300 g of powder were introduced into the powder reservoir and the coating was effected over a period of 20 min. After the heat treatment in the air circulation drying cabinet, conducted as in C1, the hollow cylindrical eggshell catalysts C10 removed from the air circulation drying cabinet, based on the total mass thereof, had an oxidic eggshell content of 10.4% by weight.

C11 (Example)

As in example C2, the finely divided powder P was mixed with $MoO_3$. In contrast to example C2, however, only about 1.9-2.1 liters of the aqueous solution (glycerol/water=1/3) were sprayed onto the support bodies within about 20 min. At the same time, within the same period, only about 8 kg of the PMo powder were metered in continuously. After the coating, as in example C2, a heat treatment was effected in the coating apparatus.

A sample of about 2 kg of coated active composition was taken. The glycerol still present in the sample was removed in an air circulation drying cabinet from Memmert GmbH+Co. KG (UM 400 type; capacity=53 l; air flow rate=800 l/h). The heat treatment conditions were identical to those of example C1. The hollow cylindrical eggshell catalysts C11 removed from the air circulation drying cabinet had, based on the total mass thereof, an oxidic eggshell content of 10% by weight.

C12 (Example)

The shaping of catalyst C12 was effected as for C1, except that, in contrast to C1, only 345.5 g of powder were introduced into the powder reservoir and the coating was effected over a period of 23 min. After the heat treatment in the air circulation drying cabinet, conducted as in C1, the hollow cylindrical eggshell catalysts C12 removed from the air circulation drying cabinet, based on the total mass thereof, had an oxidic eggshell content of 14% by weight. The active composition coverage of the inventive eggshell catalyst C12 was $0.23 \text{ mg/mm}^2$.

C13 (Example)

The shaping of catalyst C13 was effected as for C1, except that, in contrast to C1, only 360.7 g of powder were introduced into the powder reservoir and the coating was effected over a period of 24 min. After the heat treatment in the air circulation drying cabinet, conducted as in C1, the hollow cylindrical eggshell catalysts C13 removed from the air circulation drying cabinet, based on the total mass thereof, had an oxidic eggshell content of 13.4% by weight.

The properties of the catalysts according to examples C1 to C11 are shown in Table 1. The specific geometric surface area $S_m$ of the shaped support body in all examples was $0.725 \text{ mm}^2/\text{mg}$. It was calculated by dividing the geometric surface area of a shaped support body ($155.5 \text{ mm}^2$) by the mass thereof ($214.4 \text{ mg}$).

TABLE 1

| Example | $Q^{1)}$ [% by weight] | $q^{2)}$ [mg/mm$^2$] | $V_{0.02\text{-}6.5}{}^{3)}$ [ml/(g of active composition)] | $V_{0.26\text{-}2}{}^{4)}$ | $p_{vol}{}^{5)}$ | $t_B{}^{6)}$ [min] |
|---|---|---|---|---|---|---|
| C1* | 29.1 | 0.57 | 0.302 | 0.154 | 0.51 | 50 |
| C2* | 22.0 | 0.39 | 0.163 | 0.024 | 0.15 | 40 |
| C3* | 20.0 | 0.34 | 0.205 | 0.054 | 0.26 | 40 |
| C4* | 20.0 | 0.34 | 0.243 | 0.084 | 0.34 | 40 |
| C5* | 19.6 | 0.34 | 0.246 | 0.063 | 0.26 | 90 |
| C6 | 18.0 | 0.30 | 0.335 | 0.187 | 0.56 | 30 |
| C7 | 15.8 | 0.26 | 0.270 | 0.133 | 0.49 | 25 |
| C8 | 15.5 | 0.25 | 0.321 | 0.129 | 0.40 | 55 |
| C9 | 10.8 | 0.17 | 0.247 | 0.092 | 0.37 | 32 |
| C10 | 10.4 | 0.16 | 0.307 | 0.153 | 0.50 | 20 |
| C11 | 10.0 | 0.15 | 0.188 | 0.045 | 0.24 | 25 |

*noninventive
1) active composition content of the catalyst
2) active composition coverage
3) volume of the pores having mean diameters in the range from 0.26 to 2 μm
4) volume of the pores having mean diameters in the range from 0.02 to 6.5 μm
5) proportion by volume of macropores having mean diameters in the range from 0.26 to 2 μm in relation to the total pore volume in the range from 0.02 to 6.5 μm
6) duration of the coating operation In this document, all figures relating to pore characteristics of solid substances, unless explicitly stated otherwise, are based on determinations by the method of mercury porosimetry using an Auto Pore IV 9520 instrument from Micromeritics in Norcross, Ga. 30093-1877, USA. In the case of powders examined, the amount of sample introduced into the sample space in each case was 2.5 g. In the case of eggshell catalysts studied, 5 pieces of each respective eggshell catalyst were introduced into the sample space (the contribution of the pores of the geometric shaped support body of the eggshell catalyst was negligible in the cases examined compared to the contribution of the pores of the active composition shell).

The sample space continued into an elongated capillary, such that small pressure changes corresponded to distinct changes in the length of the mercury thread projecting into the capillary. The capillary volume utilized was in all cases between 25 and 91% by volume, based on the total capillary volume.

Before commencement of a particular sample analysis, the sample space (at 25° C.) was evacuated in each case down to an internal pressure of $9.3 \times 10^{-4}$ bar, and the sample was degassed at this temperature and at this pressure for 20 minutes. Thereafter, the mercury was forced into the sample space with pressures rising over time up to a final pressure of 4137 bar. The starting pressure was 0.04 bar. This corresponds to a range of pore diameters covered from 0.003 μm to 360 μm.

Figure 3:
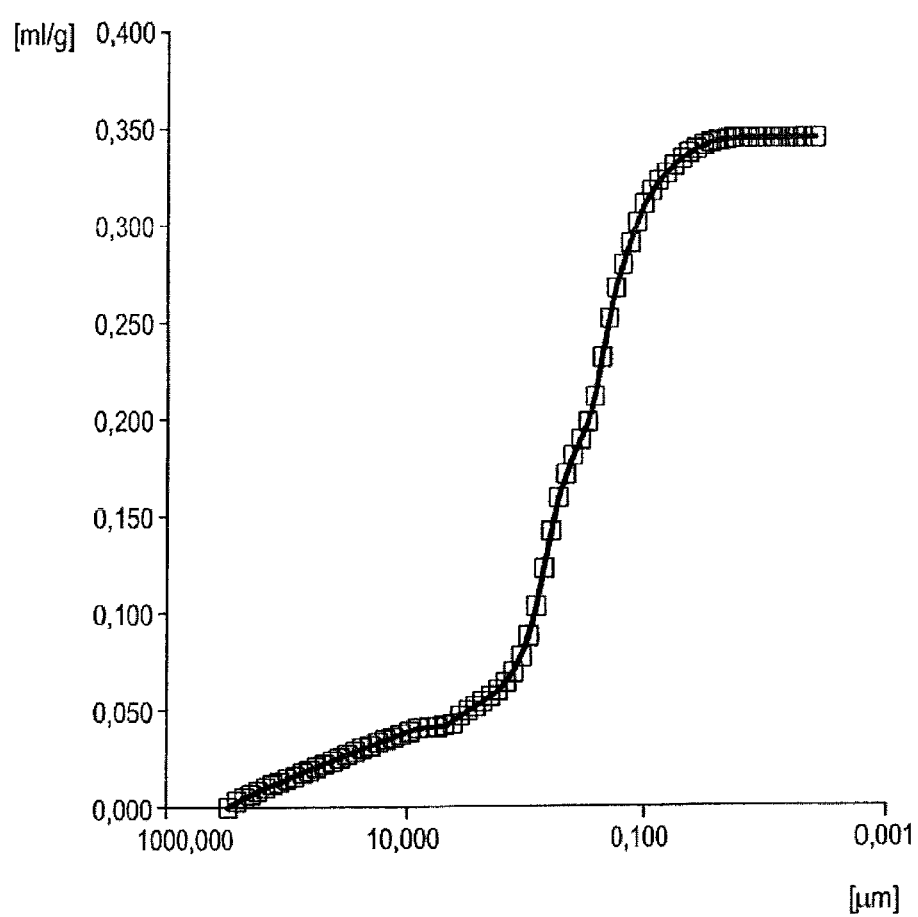
FIG. 3 shows the pore diameter distribution of the pores of the active composition shell of C1.
Figure 4:
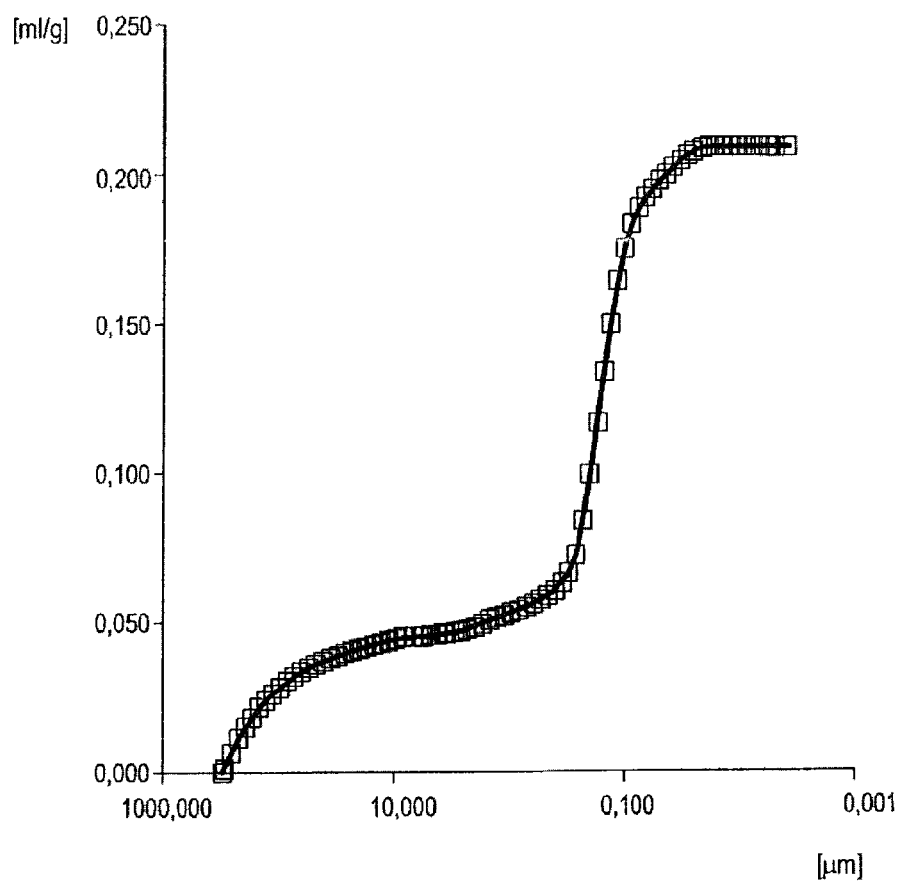
FIG. 4 shows the pore diameter distribution of the pores of the active composition shell of C2.
Figure 5:
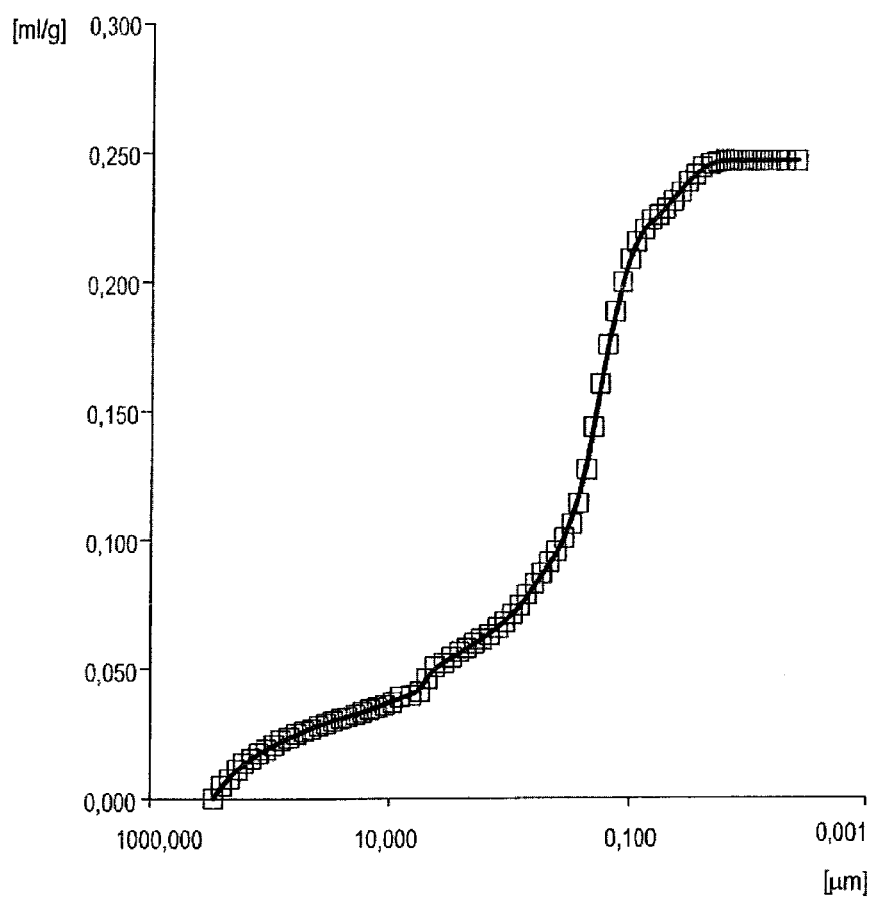
FIG. 5 shows the pore diameter distribution of the pores of the active composition shell of C3.
Figure 6:
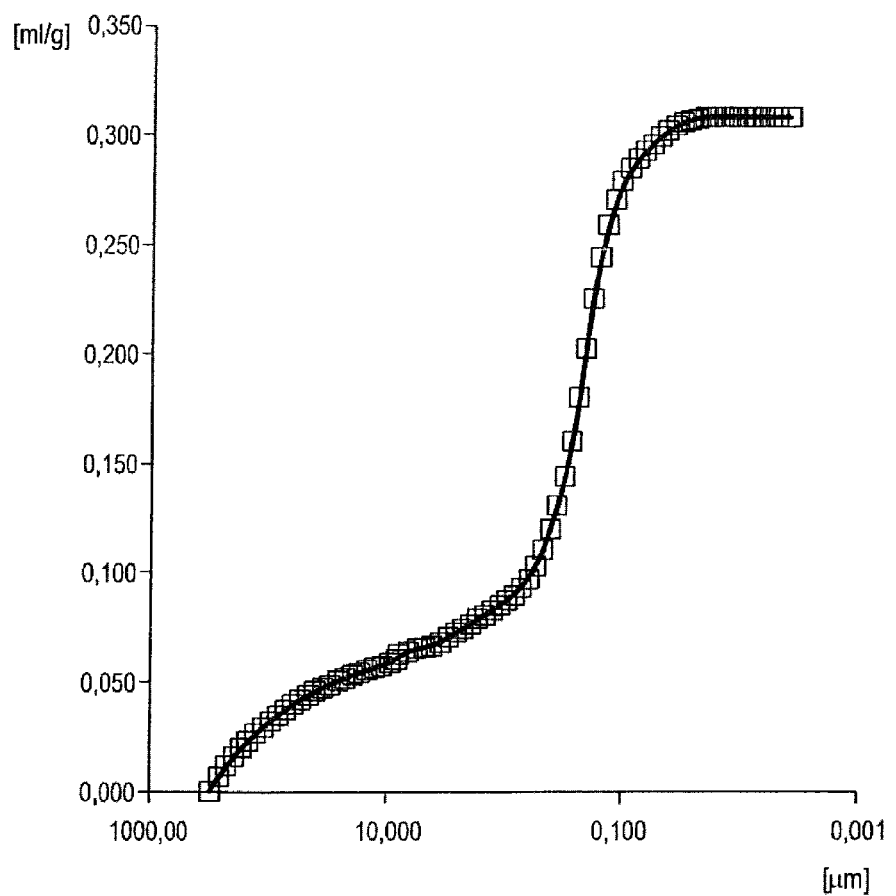
FIG. 6 shows the pore diameter distribution of the pores of the active composition shell of C4.
Figure 7:
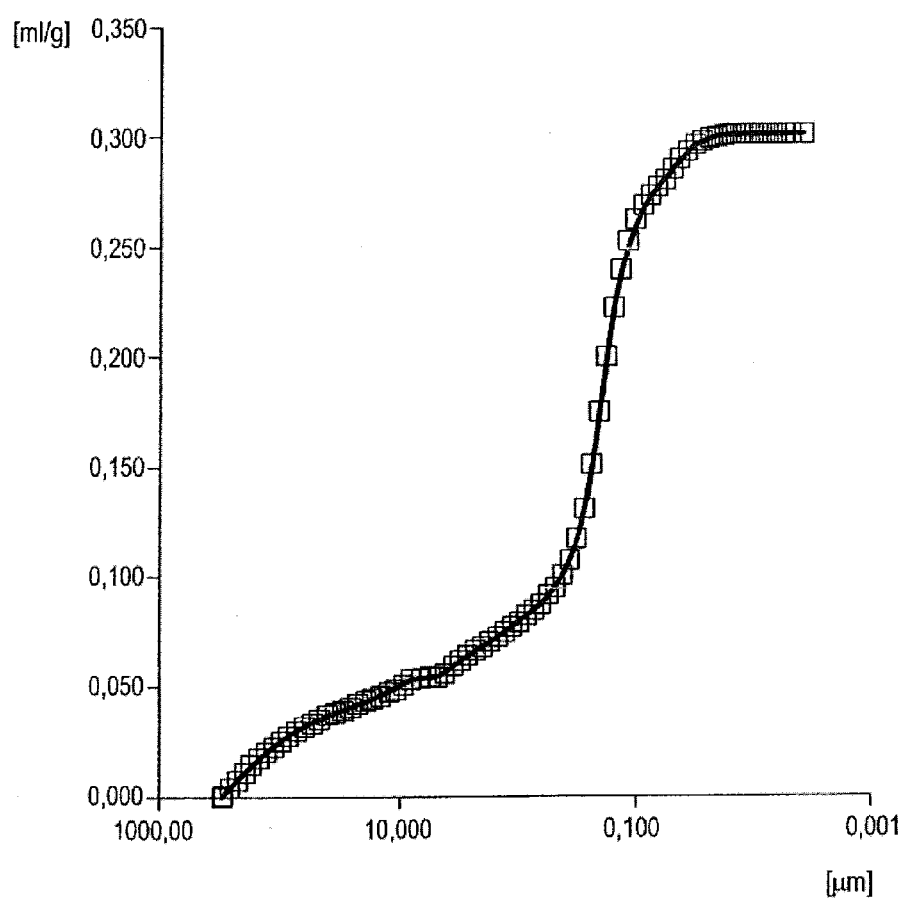
FIG. 7 shows the pore diameter distribution of the pores of the active composition shell of C5.
Figure 8:
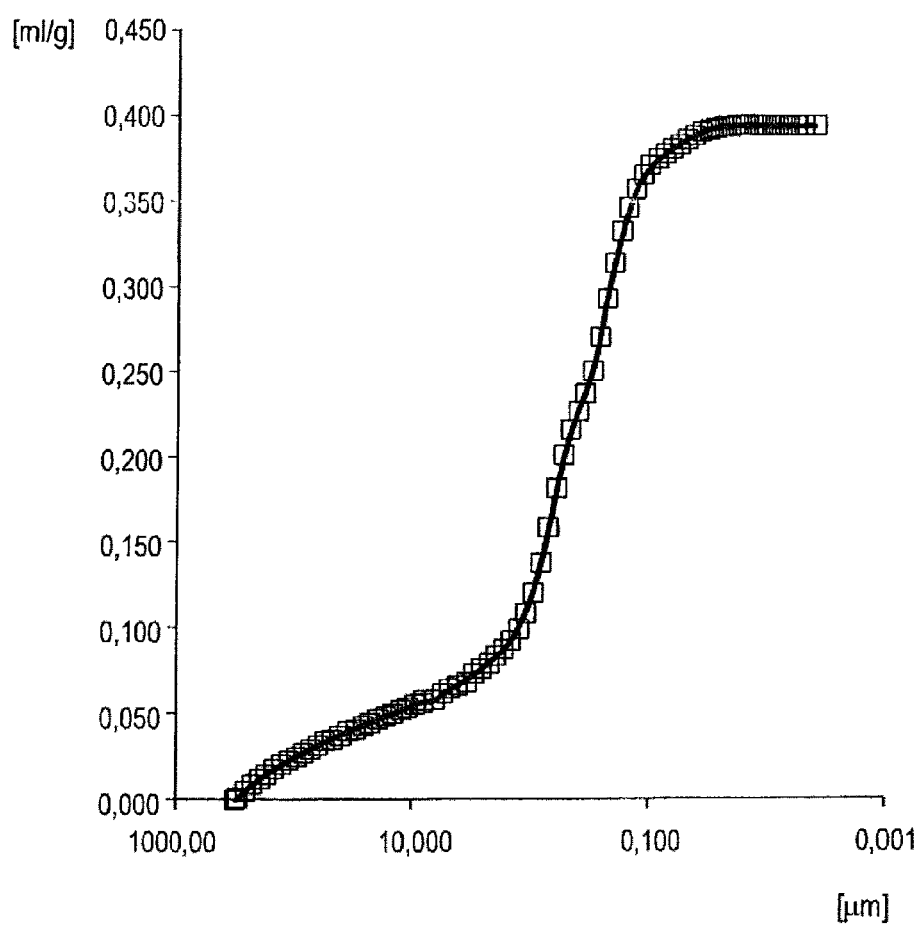
FIG. 8 shows the pore diameter distribution of the pores of the active composition shell of C6.
Figure 9:
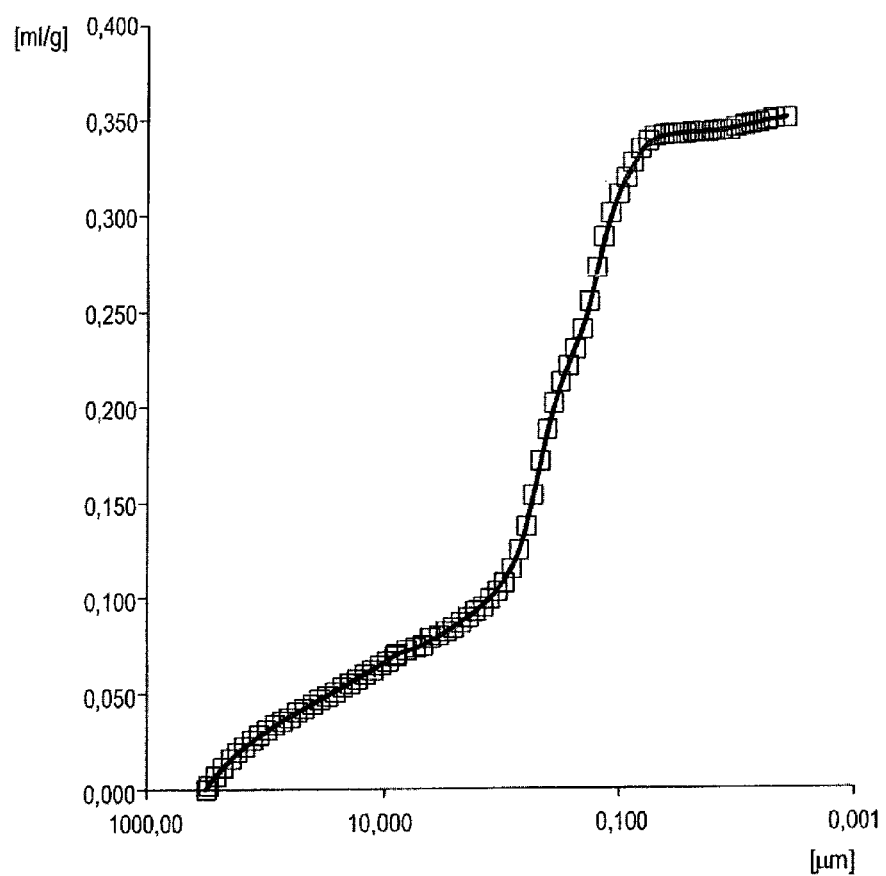
FIG. 9 shows the pore diameter distribution of the pores of the active composition shell of C7.
Figure 10:
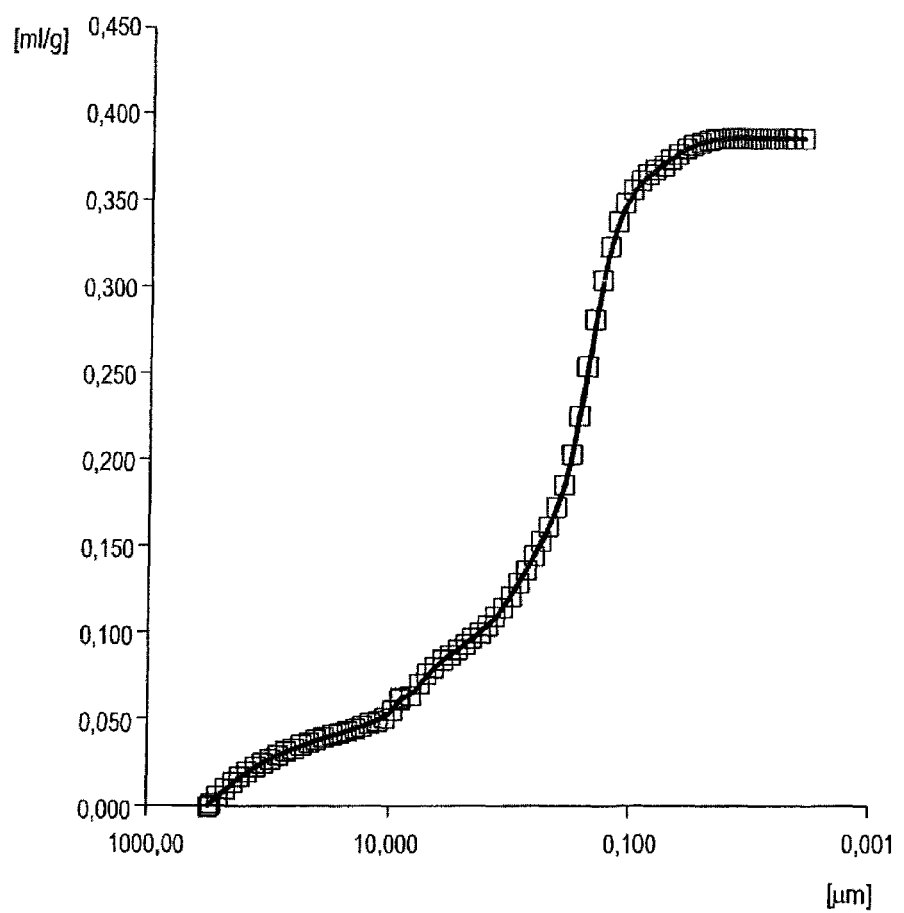
FIG. 10 shows the pore diameter distribution of the pores of the active composition shell of C8.
Figure 11:
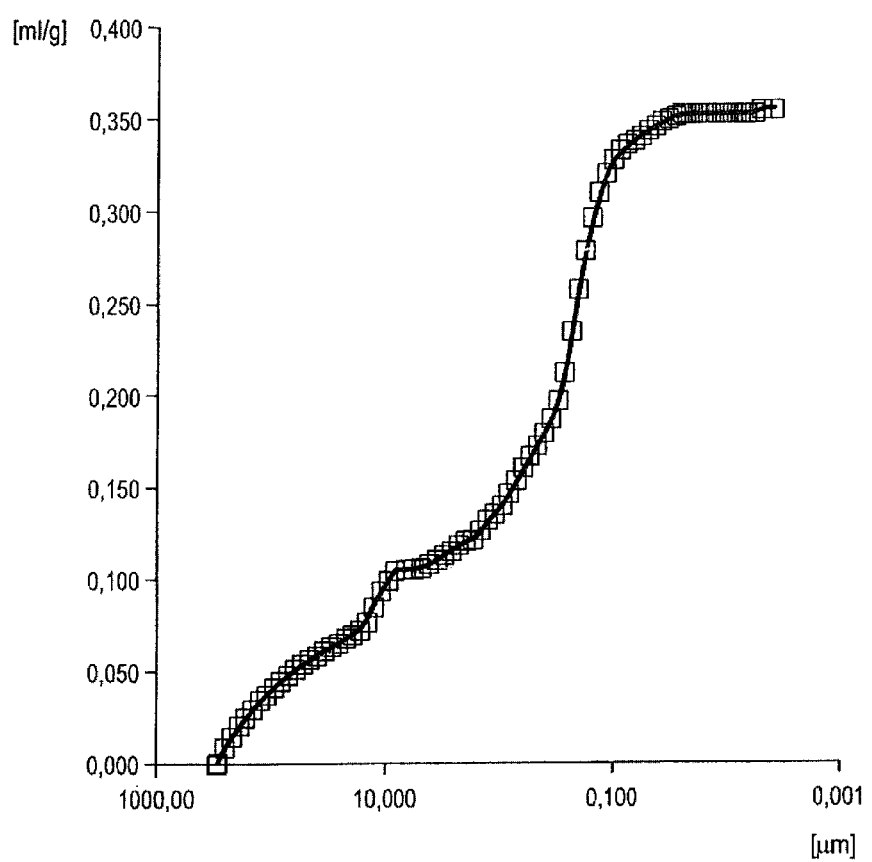
FIG. 11 shows the pore diameter distribution of the pores of the active composition shell of C9.
Figure 12:
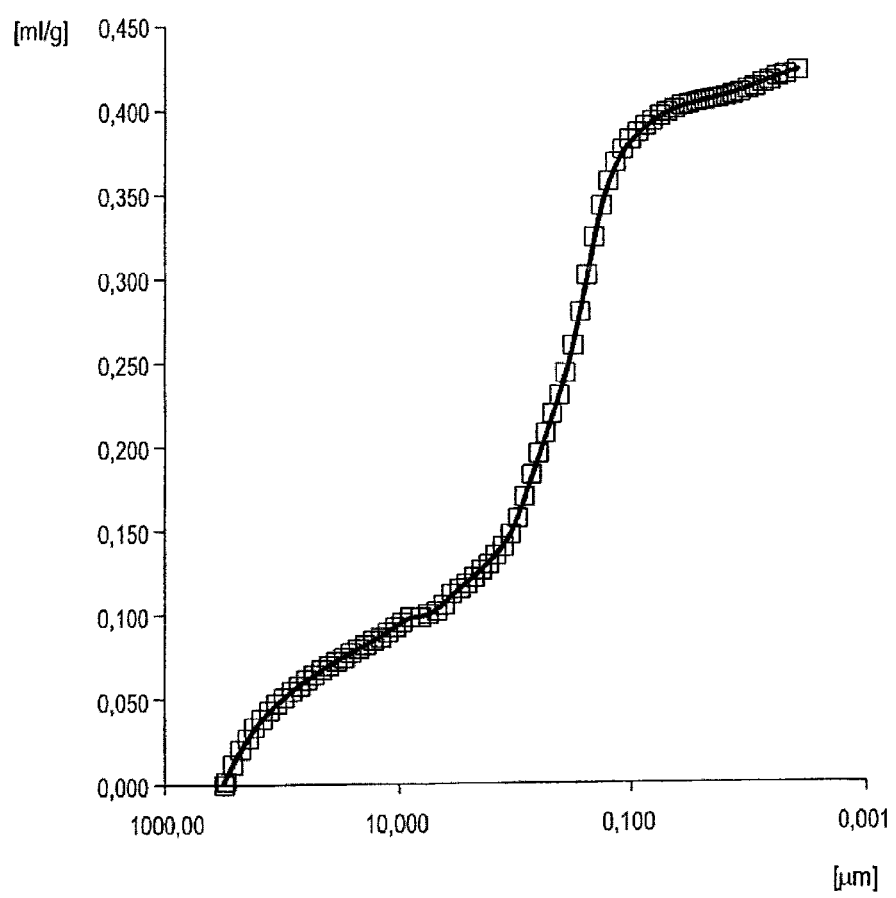
FIG. 12 shows the pore diameter distribution of the pores of the active composition shell of C10.
Figure 13:
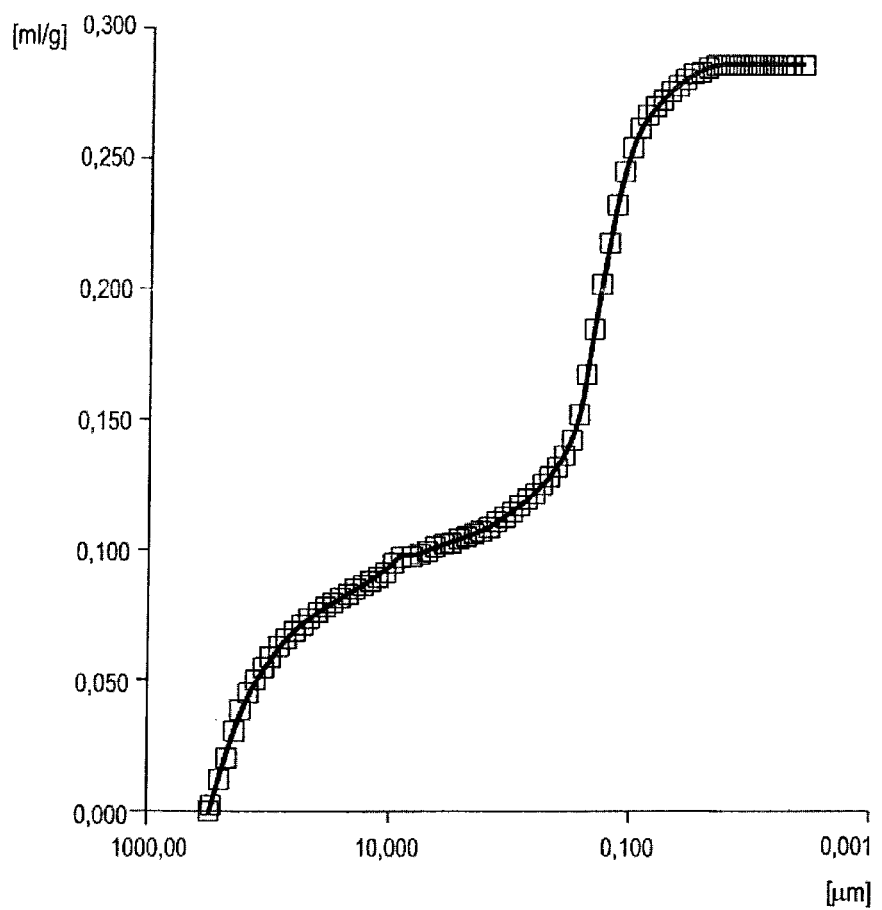
FIG. 13 shows the pore diameter distribution of the pores of the active composition shell of C11.

FIG. 3 of the present document shows the pore diameter distribution of the pores of the active composition shell of C1. Plotted on the abscissa is the respective pore diameter in μm (logarithmic plot to base 10). On the left-hand ordinate is plotted, in ([ml]/[g of active composition]), the integral over the individual contributions of the individual pore diameters to the specific total pore volume (the cumulative contribution to the aforementioned specific total pore volume) (□ curve). The end point is the (specific) total pore volume based on the active composition (total intrusion volume).

Gas Phase Oxidation of Acrolein to Acrylic Acid

A reaction tube (V2A steel; 30 mm external diameter; wall thickness 2 mm; internal diameter 26 mm; length 464 cm) comprised, from the top downward:
Section 1: length 79 cm, empty tube;
Section 2: length 62 cm, preliminary bed of steatite rings of geometry 7 mm×3 mm×4 mm (external diameter×length× internal diameter; C 220 steatite from CeramTec);
Section 3: length 100 cm, fixed catalyst bed of a homogeneous mixture consisting of 20% by weight of steatite rings of geometry 7 mm×3 mm×4 mm (external diameter× length×internal diameter; C 220 steatite from CeramTec) and 80% by weight of the respective catalyst;
Section 4: length 200 cm, fixed catalyst bed consisting exclusively of the respective catalyst used in Section 3;

Section 5: length 10 cm, downstream bed of the same steatite rings as in Section 2;

Section 6: length 14 cm, catalyst base made from V2A steel to accommodate the fixed catalyst bed.

A reaction gas mixture was conducted through the respective reaction tube, flowing through the reaction tube from the top downward, which had the following contents on entry into the reaction tube:

4.3% by volume of acrolein,
0.2% by volume of propene,
0.2% by volume of propane,
0.3% by volume of acrylic acid,
5.4% by volume of $O_2$,
7.0% by volume of $H_2O$,
0.4% by volume of CO and $CO_2$
remainder $N_2$.

The space velocity of acrolein on the fixed catalyst bed was in each case 75 l (STP)/(lh).

A stirred and externally electrically heated salt bath (mixture of 53% by weight of potassium nitrate, 40% by weight of sodium nitrite and 7% by weight of sodium nitrate, 50 kg of salt melt) flowed around the reaction tube over its length (apart from the last 10 cm of the empty tube in Section 1 and the last 3 cm of the tube in Section 6) (the flow rate in the tube was 3 m/s (in the plane at right angles to the longitudinal axis of the tube)).

The salt bath temperature $T^B$ corresponds to the temperature at which the salt melt was conducted into the salt bath. In all cases, it was set so as to result in an acrolein conversion CA of 99.3 mol % based on a single pass of the reaction mixture through the fixed catalyst bed. There was no change in the temperature of the salt bath owing to heating along the reaction tube (more heat was emitted by the salt bath than was released to the salt bath by the reaction tube). At the inlet of the reaction tube, the temperature of the reaction gas corresponded to the respective salt bath temperature $T^B$. The highest local temperature $T^H$ was determined by a point measurement in the reaction tube. The results achieved using various catalysts are summarized in Table 2.

The selectivity of acrylic acid formation ($S^{AA}$ (mol %)) is understood in this document to mean:

$$S^{AA} = \frac{\text{number of moles of acrolein converted to acrylic acid}}{\text{number of moles of acrolein converted overall}} \times 100.$$

(the conversion figures are based in each case on a single pass of the reaction gas mixture through the fixed catalyst bed).

Table 2 below shows the results resulting as a function of the eggshell catalyst used after 100 operating hours in each case:

TABLE 2

| Example | $T^B$ [° C.] | $T^H$ [° C.] | $S^{AA\ 1)}$ [mol %] |
|---|---|---|---|
| C1* | 245 | 267 | 96.7 |
| C2* | 260 | 279 | 97.0 |
| C3* | 260 | 277 | 97.1 |
| C4* | 258 | 278 | 97.1 |
| C5* | 259 | 277 | 97.2 |
| C6 | 259 | 281 | 97.7 |
| C7 | 262 | 284 | 97.7 |
| C8 | 264 | 286 | 97.5 |

TABLE 2-continued

| Example | $T^B$ [° C.] | $T^H$ [° C.] | $S^{AA\ 1)}$ [mol %] |
|---|---|---|---|
| C9 | 272 | 292 | 97.7 |
| C10 | 279 | 299 | 97.9 |
| C11 | 275 | 296 | 97.6 |

*noninventive
1) selectivity of acrylic acid formation

In the case of an inventive active composition coverage of the catalyst of not more than 0.3 mg/mm², $S^{AA}$ is 97.6 mol % or more. In the case of higher active composition coverage of the catalyst, $S^{AA}$ is lower at values of 96.7 to 97.2 mol %. The advantage of the inventive active composition coverage is established in spite of higher hotspot temperatures $T^H$ of 281-299° C.

The advantage of the high proportion by volume, preferred in accordance with the invention, of macropores ($p_m$) is manifested in the comparison of the results which have been achieved with inventive catalysts having essentially the same active composition coverage. In the group of catalysts having active composition coverage of 0.15 to 0.17 mg/mm², $S^{AA}$ is particularly high (97.9 mol %, C10), when $p_{vol}$=0.5, while $S^{AA}$ is lower (97.6 mol %, C11) when $p_{vol}$=0.24. Between the two catalysts having active composition coverage in the range from 0.25 to 0.26 mg/mm², $S^{AA}$ is high (97.7 mol %, C7), when $p_{vol}$=0.49, while $S^{AA}$ is lower (97.5 mol %, C8) when $p_{vol}$=0.40.

Gas Phase Oxidation of Acrolein to Acrylic Acid Using a Fixed Catalyst Bed with Two Successive Reaction Zones A reaction tube (stainless steel type 1.4541 (EU standard number EN 10088-3); external diameter 33.7 mm; wall thickness 2 mm; internal diameter 29.7 mm; length 400 cm, thermowell 4 mm) was charged as follows from the bottom upward:

Section 1: length 70 cm
  Upstream bed of steatite rings of geometry 7 mm×3 mm×4 mm (external diameter×length×internal diameter; C220 steatite from CeramTec);
Section 2: length 100 cm
  Fixed catalyst bed of the respective eggshell catalyst;
Section 3: length 200 cm
  Fixed catalyst bed of the respective eggshell catalyst;
Section 4: length 8 cm
  Downstream bed of the same steatite rings as in Section 1;
Section 5: length 23 cm
  Empty tube A reaction gas mixture was conducted through the respective reaction tube charged as described above, flowing through the reaction tube from the top downward, which had the following contents:

4.5% by volume of acrolein,
0.1% by volume of propene,
0.07% by volume of propane,
0.5% by volume of acrylic acid,
5.4% by volume of $O_2$,—calculate
7% by volume of $H_2O$,—calculate
0.6% by volume of CO and $CO_2$, and
remainder $N_2$.

The space velocity of acrolein on the fixed catalyst bed (as defined in DE-A 19927624) was in each case 75 l (STP)/(lh).

A stirred and externally electrically heated salt bath (mixture of 53% by weight of potassium nitrate, 40% by weight of sodium nitrite and 7% by weight of sodium nitrate; 50 kg of salt melt) flowed around the reaction tube over its length (the flow rate in the tube was 3 m/s (in the plane at right angles to the longitudinal axis of the tube)).

The salt bath temperature $T^B$ (° C.) (with which the salt bath was supplied) was adjusted in all cases so as to result in an acrolein conversion, based on a single pass of the reaction gas mixture through the fixed catalyst bed, of 98.3 mol %. There was no change in the salt bath temperature along the reaction tube owing to heating (more heat was emitted by the salt bath than was released from the reaction tube to the salt bath). The feed temperature of the reaction gas mixture (at the inlet into the reaction tube) was adjusted in each case to the respective salt bath temperature.

The temperature in the catalyst bed was measured continuously by means of a thermocouple which had been positioned in a thermowell within the interior of the reactor tube and which had been moved from the bottom upward within the reactor bed with the aid of a pulling machine. The maximum temperature in this measurement corresponded to the hotspot temperature $T^H$.

Table 3 below shows the results resulting after 100 hours of operation, which are established after charging reactor sections 2 and 3 with different inventive and noninventive eggshell catalysts.

TABLE 3

| | Reactor charge | | $T^B$ [° C.] | $T^H$ [° C.] | $X^{H***}$ [cm] | $S^{AA}$ [mol %] |
|---|---|---|---|---|---|---|
| | Section 2 | Section 3 | | | | |
| Comparative example | 70% by weight of C3*, 30% by weight of steatite rings** | 100% by weight of C3* | 263 | 312 | 61 | 97.0 |
| D1 | 100% by weight of C10 | 100% by weight of C8 | 264 | 309 | 74 | 98.3 |
| D2 | 100% by weight of C12 | 100% by weight of C3* | 261 | 313 | 81 | 97.5 |

*noninventive
**steatite rings of geometry 7 mm × 3 mm × 4 mm (C220 steatite from CeramTec)
***distance of the hotspot present in Section 2 from the transition from Section 1 to Section 2

The comparison of example D2 with the comparative example in Table 3 indicates, through the better acrylic acid selectivity (97.5 mol %) of D2 compared to the reference (97 mol %) that the charging of that reaction zone having the highest temperature (the hotspot is in D2 and the reference in Section 2, see Table 3) with inventive eggshell catalysts is advantageous with regard to the selectivity of acrylic acid formation.

Partial Exchange of the Upstream Reaction Zone of a Food Catalyst Bed

DE-A 10232748 describes the exchange of a portion of the fixed catalyst bed for a fresh catalyst charge. It was examined hereinafter whether the inventive catalysts are also advantageous for the partial exchange of a fixed catalyst bed described in DE-A 10232748.

A reaction tube (stainless steel type 1.4541 (EU standard number EN 10088-3); external diameter 33.7 mm; wall thickness 2 mm; internal diameter 29.7 mm; length 400 cm, thermowell 4 mm) was charged from the bottom upward as follows:

Section 1: length 75 cm
  Upstream bed of steatite rings of geometry 7 mm×3 mm×4 mm (external diameter×length×internal diameter; C220 steatite from CeramTec);

Section 2: length 110 cm
  Fixed catalyst bed of the respective eggshell catalyst;
Section 3: length 190 cm
  Fixed catalyst bed consisting of eggshell catalyst (71% by weight) prepared according to working example 1 of DE 103 60 057 A1 and 29% by weight of steatite rings of geometry 7 mm×3 mm×4 mm (external diameter×length×internal diameter; C220 steatite from CeramTec);
Section 4: length 3 cm
  Downstream bed of the same steatite rings as in Section 1;
Section 5: length 23 cm
  Empty tube A reaction gas mixture was conducted through the respective reaction tube charged as described above, flowing through the reaction tube from the top downward, which had the following contents:
4.5% by volume of acrolein,
0.1% by volume of propene,
0.07% by volume of propane,
0.5% by volume of acrylic acid,
5.4% by volume of $O_2$,
7% by volume of $H_2O$,
0.6% by volume of CO and $CO_2$, and
remainder $N_2$.

The space velocity of acrolein on the fixed catalyst bed (as defined in DE-A 19927624) was in each case 75 l (STP)/(lh).

A stirred and externally electrically heated salt bath (mixture of 53% by weight of potassium nitrate, 40% by weight of sodium nitrite and 7% by weight of sodium nitrate; 50 kg of salt melt) flowed around the reaction tube over its length (the flow rate in the tube was 3 m/s (in the plane at right angles to the longitudinal axis of the tube)).

The salt bath temperature $T^B$ (° C.) (with which the salt bath was supplied) was adjusted in all cases so as to result in an acrolein conversion, based on a single pass of the reaction gas mixture through the fixed catalyst bed, of 99.3 mol %. There was no change in the salt bath temperature along the reaction tube owing to heating (more heat was emitted by the salt bath than was released from the reaction tube to the salt bath). The feed temperature of the reaction gas mixture (at the inlet into the reaction tube) was adjusted in each case to the respective salt bath temperature. The temperature in the catalyst bed was measured continuously by means of a thermocouple which had been positioned in a thermowell within the interior of the reactor tube and which had been moved from the bottom upward within the reactor bed with the aid of a pulling machine. The maximum temperature in this measurement corresponded to the hotspot temperature $T^H$.

Table 4 below shows the results resulting after 100 hours of operation, which are established after charging reactor section 2 with inventive and noninventive eggshell catalysts.

TABLE 4

| | Section 2 | $T^B$ [° C.] | $T^H$ [° C.] | $X^{H***}$ [cm] | $S^{AA}$ [mol %] |
|---|---|---|---|---|---|
| Comparative example | 50% by weight of C2*, 50% by weight of steatite rings** | 274 | 330 | 46 | 96.9 |
| E1 | 100% by weight of C11 | 275 | 324 | 71 | 97.5 |

*noninventive
**steatite rings of geometry 7 mm × 3 mm × 4 mm (C220 steatite from CeramTec)
***distance of the hotspot present in section 2 from the transition from section 1 to section 2

The comparison of example E1 with the comparative example in Table 4 indicates, through the better acrylic acid selectivity (97.5 mol %) of example E1 compared to the reference (96.9 mol %) that, in the event of a partial catalyst exchange, the filling of the upstream reaction zone with inventive eggshell catalysts is advantageous with regard to the selectivity of acrylic acid formation.

Gas Phase Oxidation of Acrolein to Acrylic Acid Using a Fixed Catalyst Bed with Two Successive Heating Zones A reaction tube (stainless steel type 1.4541 (EU standard number EN 10088-3); external diameter 33.7 mm; wall thickness 2 mm; internal diameter 29.7 mm; length 400 cm, thermowell 4 mm) was charged from the top downward as follows:

Section 1: length 70 cm
    Upstream bed of steatite rings of geometry 7 mm×3 mm×4 mm (external diameter×length×internal diameter; C220 steatite from CeramTec);
Section 2: length 100 cm
    Fixed catalyst bed of eggshell catalyst C13;
Section 3: length 200 cm
    Fixed catalyst bed of eggshell catalyst C3;
Section 4: length 8 cm
    Downstream bed of the same steatite rings as in Section 1;
Section 5: length 23 cm
    Empty tube A reaction gas mixture was conducted through the respective reaction tube charged as described above, flowing through the reaction tube from the top downward, which had the following contents:

4.5% by volume of acrolein,
0.1% by volume of propene,
0.07% by volume of propane,
0.5% by volume of acrylic acid,
5.4% by volume of $O_2$,
7% by volume of $H_2O$,
0.6% by volume of CO and $CO_2$, and
remainder $N_2$.

The space velocities of acrolein on the fixed catalyst bed $L^{ACR}$ (as defined in DE-A 19927624) were 75, 100 and 145 $l_{Acrolein}$ (STP)/(lh).

The reaction tube was heated with two different salt baths, as described in DE 2010-10048405. The first 190 cm were thermostated with a salt bath pumped at countercurrent flow which was supplied at temperature $T^A$. The second 210 cm were thermostated with a salt bath B pumped at countercurrent flow which was supplied at temperature $T^B$. Both salt baths consisted of a mixture of 53% by weight of potassium nitrate, 40% by weight of sodium nitrite and 7% by weight of sodium nitrate, 50 kg of salt melt. The flow rate in the tube was 3 m/s (in the plane at right angles to the longitudinal axis of the tube).

The salt bath temperatures $T^A$ and $T^B$ (° C.) (with which both salt baths were supplied) wer adjusted in all cases so as to result in an acrolein conversion, based on a single pass of the reaction gas mixture through the fixed catalyst bed, of 99.4 mol % at space velocities of acrolein of 75 and 100 $l_{Acrolein}$ (STP)/(lh) and 98.5 mol % at space velocity of acrolein of 145 $l_{Acrolein}$ (STP)/(lh). There was no change in the salt bath temperature along the reaction tube owing to heating (more heat was emitted by the salt bath than was released from the reaction tube to the salt bath). The feed temperature of the reaction gas mixture (at the inlet into the reaction tube) was adjusted in each case to the respective salt bath temperature.

The temperature in the catalyst bed was measured continuously by means of a thermocouple which had been positioned in a thermowell within the interior of the reactor tube and which had been moved from the bottom upward within the reactor bed with the aid of a pulling machine. The peak temperatures found in this measurement corresponded to the hotspot temperatures $T^{H1}$ and $T^{H2}$, respectively.

Table 5 below shows the results resulting after 100 hours of operation, which are established at different space velocities with inventive eggshell catalyst.

TABLE 5

| Reactor charge | | $L^{ACR}$ | | | | | | | |
|---|---|---|---|---|---|---|---|---|---|
| Section 2 | Section 3 | [l (STP)/(lh)] | $T^A$ [° C.] | $T^B$ [° C.] | $T^{H1}$ [° C.] | $X^{H1}$* [cm] | $T^{H2}$ [° C.] | $X^{H2}$** [cm] | $S^{AS}$ [mol %] |
| F1 100% by weight C13 | 100% by weight C3 | 75 | 263 | 263 | 314 | 91 | No second peak detected | | 96.5 |
| F2 100% by weight C13 | 100% by weight C3 | 100 | 265 | 269 | 314 | 95 | 307 | 145 | 96.1 |
| F3 100% by weight C13 | 100% by weight C3 | 145 | 272 | 273 | 320 | 110 | 323 | 135 | 95.8 |

*distance of the first hotspot from the transition from section 1 to section 2
**distance of the second hotspot from the transition from section 1 to section 2

The invention claimed is:

1. A catalyst for the preparation of an α,β-unsaturated carboxylic acid by gas phase oxidation of an α,β-unsaturated aldehyde, comprising a shaped support body with an active composition applied thereto, wherein the active composition coverage q $$q = \frac{Q}{(100 - Q)S_m}$$

is at most 0.3 mg/mm², where Q is the active composition content of the catalyst in % by weight and $S_m$ is the specific geometric surface area of the shaped support body in mm²/mg.

2. The catalyst according to claim 1, wherein the proportion by volume $p_{vol}$ of macropores is at least 0.35, where $p_{vol}$ is determined by $$p_{vol} = \frac{V_{0.26-2}}{V_{0.02-6.5}}$$

in which $V_{0.26-2}$ is the volume of the pores having a mean diameter of from 0.26 to 2 μm, and $V_{0.02-6.5}$ is the volume of the pores having a mean diameter of from 0.02 to 6.5 μm.

3. The catalyst according to claim 1, wherein the shaped support body is a hollow cylindrical shaped support body.

4. The catalyst according to claim 1, wherein the shaped support body comprises steatite and is essentially nonporous.

5. The catalyst according to claim 3, wherein the hollow cylindrical shaped support body has a height of from 2 to 5 mm and an external diameter of from 4 to 8 mm, and the median difference between the external diameter and internal diameter is from 1 to 2 mm.

6. The catalyst according to claim 1, wherein the active composition comprises a multielement oxide of formula (II)

$$Mo_{12}V_aW_bCu_cX^4_eX^5_fO_n \qquad (II),$$

in which $X^4$ is one or more alkali metals and/or alkaline earth metals, $X^5$ is one or more elements from the group consisting of Si, Al, Ti and Zr, a is a number in the range from 2 to 4, b is a number in the range from 0 to 3, c is a number in the range from 0.8 to 3, e is a number in the range from 0 to 4, f is a number in the range from 0 to 40, and n is the stoichiometric coefficient of the element oxygen, which is determined by the stoichiometric coefficients of the elements other than oxygen and the valency thereof in (II).

7. A method for preparing the catalyst according to claim 1, said method comprising coating the shaped support body with the active composition, wherein the coating comprises mixing a multitude of shaped support bodies, a pulverulent active composition and a liquid binder, without saturating the pulverulent active composition with the liquid binder, in a vessel, wherein the duration of the coating operation is less than 30 minutes.

8. The method according to claim 7, wherein the shaped support bodies are initially charged in the vessel and the pulverulent active composition and the liquid binder are added to the vessel separately from one another over the duration of the coating.

9. The method according to claim 7, wherein the mixing is effected by continuous movement of the vessel.

10. The method according to claim 9, wherein the movement is a rotational movement.

11. The method according to claim 7, wherein the pulverulent active composition has a numerical proportion of particles having a longest dimension above 50 μm of less than 1%.

12. A method for preparing an α,β-unsaturated carboxylic acid by gas phase oxidation of an α,β-unsaturated aldehyde with molecular oxygen over a fixed catalyst bed, wherein the fixed catalyst bed comprises a bed of the catalyst according to claim 1.

13. The method according to claim 12, wherein the fixed catalyst bed comprises at least two successive reaction zones, and the bed, at least in the reaction zone that is closest to the reactor inlet, comprises the catalyst.

14. The method according to claim 12, wherein the fixed catalyst bed comprises at least two successive reaction zones, and the bed, at least in the reaction zone in which the highest local temperature occurs, comprises the catalyst.

15. The method according to claim 12, wherein, after a certain operating time, a portion of the bed in which the highest local temperature occurs is removed and replaced by a fresh bed.

16. The method according to claim 12, wherein the α,β-unsaturated aldehyde is acrolein and the α,β-unsaturated carboxylic acid is acrylic acid.

* * * * *